(12) United States Patent
Mori et al.

(10) Patent No.: US 8,164,659 B2
(45) Date of Patent: Apr. 24, 2012

(54) IMAGE PICKUP APPARATUS, IMAGE DISPLAY APPARATUS, AND IMAGE DISPLAY SYSTEM

(75) Inventors: Takeshi Mori, Machida (JP); Satomi Kobayashi, Tokyo (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 579 days.

(21) Appl. No.: 12/337,165

(22) Filed: Dec. 17, 2008

(65) Prior Publication Data

US 2009/0167908 A1 Jul. 2, 2009

Related U.S. Application Data

(60) Provisional application No. 61/014,190, filed on Dec. 17, 2007.

(51) Int. Cl.
*H04N 9/64* (2006.01)
*H04N 5/222* (2006.01)
*H04N 7/18* (2006.01)

(52) U.S. Cl. .................. 348/245; 348/333.12; 348/65

(58) Field of Classification Search .............. 348/65, 348/241–251
See application file for complete search history.

(56) References Cited

U.S. PATENT DOCUMENTS

| 5,748,801 A | 5/1998 | Goto |
| 2006/0098941 A1* | 5/2006 | Abe et al. .................. 386/52 |
| 2007/0165120 A1* | 7/2007 | Takane .................. 348/248 |

FOREIGN PATENT DOCUMENTS

| JP | 2003-070728 | 3/2003 |
| JP | 2006-295346 | 10/2006 |
| JP | 2007-019820 | 1/2007 |

OTHER PUBLICATIONS

Hirakawa Katsumi; Image Display Apparatus; Jun. 15, 2006; English machine translation of Japanese pub # 2006149684.*

* cited by examiner

*Primary Examiner* — Sinh Tran
*Assistant Examiner* — Shahbaz Nazrul
(74) *Attorney, Agent, or Firm* — Scully, Scott, Murphy & Presser, P.C.

(57) ABSTRACT

An image display system has a capsule endoscope for capturing an in-vivo image of a subject, a receiving device for receiving the in-vivo image from the capsule endoscope, and an image display apparatus for displaying a group of in-vivo images of the subject. The capsule endoscope has an imaging unit having a black region which optical rays do not reach in an effective pixel region contributing to image capture. By the imaging unit, an in-vivo image including the signal level of the black region is detected. The receiving device receives an image signal of the in-vivo image. The image display apparatus obtains an in-vivo image group from the receiving device. The image display apparatus does not display an in-vivo image in the in-vivo image group determined as an image influenced by fluctuations in the power source voltage but displays a stable in-vivo image which is not influenced by fluctuations in the power source voltage.

10 Claims, 20 Drawing Sheets

IMAGE PICKUP APPARATUS, IMAGE DISPLAY APPARATUS, AND IMAGE DISPLAY SYSTEM

BACKGROUND OF THE INVENTION

1. Field of the Invention

The present invention relates to an image pickup apparatus, an image display apparatus, and an image display system capable of preventing an image influenced by fluctuations in an output of a power source from being displayed.

2. Description of the Related Art

Hitherto, there is an image pickup apparatus for obtaining image data of a subject by photoelectrically converting an optical subject image formed by an optical system such as a lens. The image pickup apparatus generally has therein a solid-state imaging device such as a CCD or CMOS. The image pickup apparatus consumes power supplied from a predetermined power source, makes the solid-state imaging device perform the photoelectric converting process and, as a result, obtains an image of a subject. The image of the subject obtained by the image pickup apparatus is supplied to an image display apparatus or the like, and is displayed on a display.

Such image pickup apparatuses include an image pickup apparatus for correcting, for example, the black level of an image based on a signal level detected in an optical black region as a pixel region to which light from a lens is not always applied (refer to Japanese Patent Application Laid-open No. 2006-295346) and an image pickup apparatus for capturing an image of the inside of an organ of a subject (hereinbelow, also called an in-vivo image) by a solid-state imaging device provided in a capsule casing formed in a size which can be introduced into the organs of a subject (refer to Japanese Patent Application Laid-open No. 2003-70728). For example, there is also a solid-state imaging device built in such an image pickup apparatus, in which optical black regions are scattered about within an effective pixel region for generating an output signal of a captured image (refer to Japanese Patent Application Laid-open No. 2007-19820).

In an image pickup apparatus for capturing an image of a subject by consuming power from a predetermined power source as described above, there is a case that supply of power becomes insufficient due to fluctuations in output of the power source or exhaustion of a battery which is internally provided as the power source. As a result, fluctuations in the power source voltage supplied to an image pickup system such as a solid-state imaging device in the image pickup apparatus increase. Due to the fluctuations in the power source voltage, there is a case that an image of a subject captured by the image pickup apparatus is influenced. The influence on an image, of the fluctuations in the power source voltage varies according to the circuit configuration in an image pickup apparatus. For example, there is a case that the black reference level in an image is not uniform but is non-uniform in an entire display image due to such fluctuations in the power source voltage.

However, in the above-described conventional techniques, it is difficult to stop outputting image data influenced by fluctuations in the power source voltage of an image pickup apparatus in enormous image data captured by the image pickup apparatus, that is, image data influenced by fluctuations in the black reference level. There is, consequently, a problem that it is difficult to provide a stable image to the user without displaying an image influenced by fluctuations in the power source voltage of the image pickup apparatus.

SUMMARY OF THE INVENTION

An image pickup apparatus according to an aspect of the present invention includes an imaging unit having a black region which optical rays do not reach in a pixel region on an imaging device, for capturing an image by photoelectrically converting light information received via the pixel region and detecting signal level of the black region; and an image determining unit for performing an image determining process on each of the images by calculating pixel information of the black region where changes as output of a power source for supplying power to the imaging unit fluctuates based on the signal level of the black region in each of images captured by the imaging unit, and comparing the calculated pixel information with a predetermined threshold, and inhibiting output of the image based on a result of determination of the image determining process.

An image display apparatus according to another aspect of the present invention includes an image obtaining unit for obtaining a series of images captured by an imaging unit having a black region where optical rays do not reach in a pixel region on an imaging device and including a signal level of the black region in each of the images; a display unit capable of displaying the series of images; an image determining unit for performing an image determining process on each of the images by calculating pixel information of the black region based on the signal level of the black region in each of the images included in the series of images, and comparing the calculated pixel information with a predetermined threshold, and inhibiting output of an image based on a result of determination of the image determining process; and a display control unit for displaying the series of images except for the image inhibited to be output by the image determining unit on the display unit.

An image display system according to still another aspect of the present invention includes an imaging unit having a black region where optical rays do not reach, in a pixel region on an imaging device, for capturing an image by photoelectrically converting light information received via the pixel region and detecting signal level of the black region; a display unit capable of displaying a series of images captured by the imaging unit; an image determining unit for performing an image determining process on each of the images by calculating pixel information of the black region based on the signal level of the black region in each of images included in the series of images and comparing the calculated pixel information with a threshold, and inhibiting output of the image based on a result of determination of the image determining process; and a display control unit for displaying, on the display unit, the series of images except for the image inhibited to be output by the image determining unit.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Preferred embodiments of an image pickup apparatus, an image display apparatus, and an image display system according to the present invention will be described in detail hereinbelow with reference to the drawings. In the following, a capsule endoscope for capturing an in-vivo image of a subject will be described as an example of the image pickup apparatus. However, the present invention is not limited to the embodiments.

First Embodiment

Figure 1:
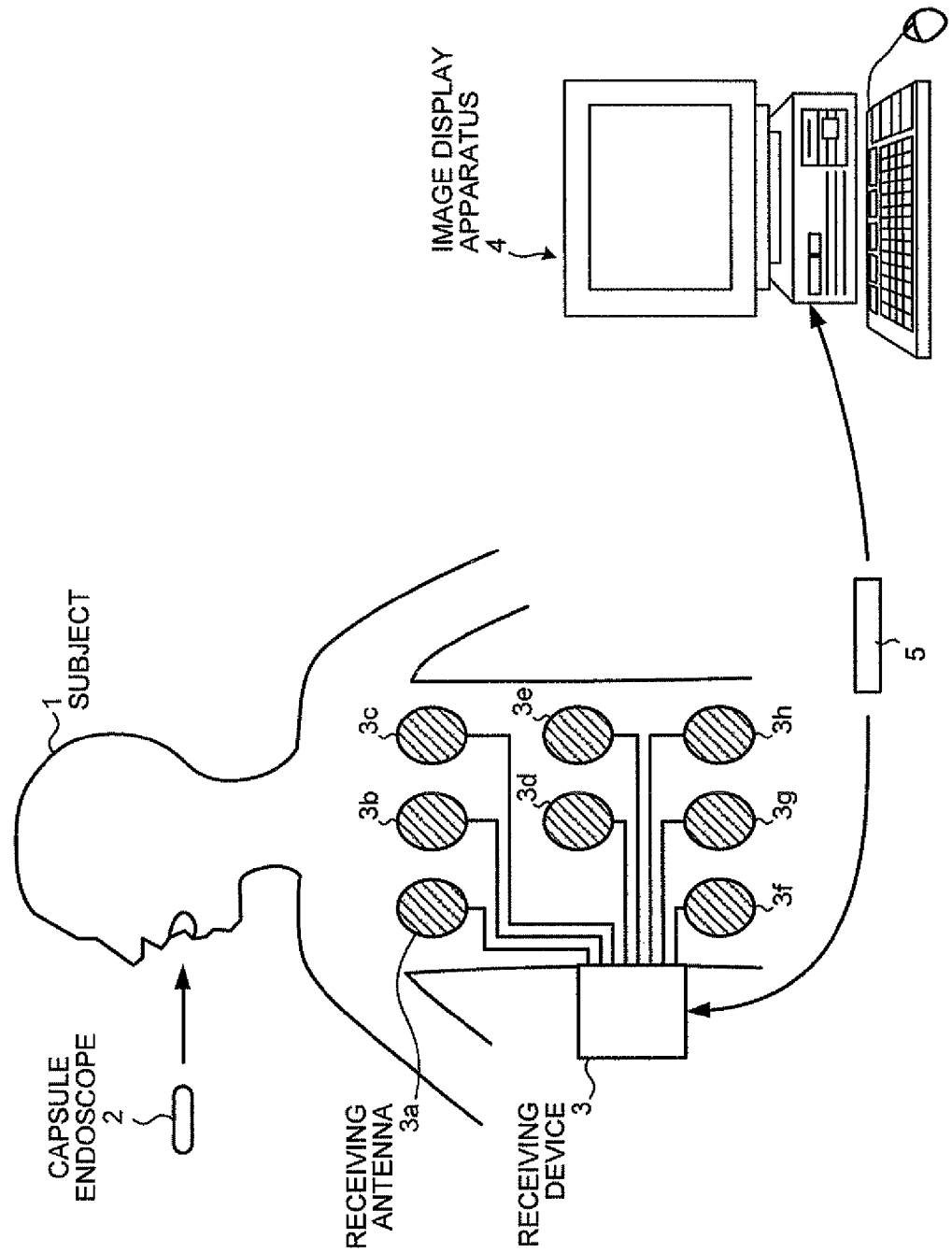
FIG. 1 is a schematic view illustrating a configuration example of an image display system as a first embodiment of the present invention.

FIG. 1 is a schematic view illustrating a configuration example of an image display system as a first embodiment of the present invention. As shown in FIG. 1, an image display system as the first embodiment of the present invention includes a capsule endoscope 2 for capturing an in-vivo image of a subject 1, a receiving device 3 for receiving the in-vivo image of the subject 1 captured by the capsule endoscope 2, an image display apparatus 4 for displaying various information such as an in-vivo image of the subject 1, and a portable recording medium 5 for transferring data between the receiving device 3 and the image display apparatus 4.

The capsule endoscope 2 is an example of the image pickup apparatus according to the present invention and has, in a capsule casing, an imaging function and a radio communication function. Concretely, the capsule endoscope 2 is introduced to the inside of the subject 1 by oral intake or the like and, after that, moves in organs of the subject 1 by peristaltic movement or the like. For a period since the capsule endoscope 2 is introduced into the organs of the subject 1 until it is naturally ejected to the outside of the subject 1, the capsule endoscope 2 sequentially captures in-vivo images of the subject 1 at predetermined intervals (for example, 0.5 second intervals). The capsule endoscope 2 wirelessly transmits the series of in-vivo images of the subject 1 which are time-sequentially captured, to the receiving device 3 outside the subject 1. To the capsule endoscope 2, identification information (ID information) to identify each of capsule endoscopes is assigned. The capsule endoscope 2 wirelessly transmits the ID information of itself together with the in-vivo images of the subject 1 to the receiving device 3.

The receiving device 3 receives the series of in-vivo images of the subject 1 captured by the capsule endoscope 2 in the subject 1. Concretely, the receiving device 3 has a plurality of receiving antennas 3a to 3h disposed dispersedly on the body surface of the subject 1, and receives a radio signal from the capsule endoscope 2 via the plurality of receiving antennas 3a to 3h. The receiving device 3 performs a demodulating process or the like on the radio signal from the capsule endoscope 2 and, as a result, obtains the in-vivo images of the subject 1 and the ID information and the like of the capsule endoscope 2. In the receiving device 3, the portable recording medium 5 is detachably inserted. The receiving device 3 records the series of in-vivo images and the ID information of the subject 1 obtained from the capsule endoscope 2 onto the portable recording medium 5. In this case, the receiving device 3 records time information indicative of image capture time of the in-vivo images of the subject 1 in association with the in-vivo images onto the portable recording medium 5.

The receiving antennas 3a to 3h are realized by using loop antennas or the like and disposed dispersedly at predetermined positions on the body surface of the subject 1, for example, positions corresponding to a movement path (that is, the digestive tract) of the capsule endoscope 2 in the subject 1. The receiving antennas 3a to 3h are connected to the above-described receiving device 3, capture the radio signals transmitted by the capsule endoscope 2 in the subject 1, and transmits the captured radio signals to the receiving device 3. On the subject 1, it is sufficient to dispose at least one receiving antenna for transmitting the radio signal from the capsule endoscope 2 to the receiving device 3. The number of capsule endoscopes 2 is not particularly limited to eight. The receiving antennas 3a to 3h may be also dispersedly disposed in predetermined positions of a jacket which is put on the subject 1.

The portable recording medium 5 is a recording medium which can be carried for transfer of data between the receiving device 3 and the image display apparatus 4. The portable recording medium 5 can be detachably inserted in the receiving device 3 and the image display apparatus 4. The portable recording medium 5 has a structure with which data can be output and recorded from/to any of the receiving device 3 and the image display apparatus 4 when inserted. Concretely, in the case where the portable recording medium 5 is inserted in the receiving device 3, it records various data such as a series of in-vivo images of the subject 1 received by the receiving device 3, the time information of the in-vivo images, and ID information of the capsule endoscope 2. On the other hand, in the case where the portable recording medium 5 is inserted in the image display apparatus 4, the portable recording medium 5 outputs the recording data such as the series of in-vivo images of the subject 1, the time information of the in-vivo images, and the ID information of the capsule endoscope 2 to the image display apparatus 4. In such a manner, the recording data of the portable recording medium 5 is taken by the image display apparatus 4. On the portable recording medium 5, patient information and the like on the subject 1 in which the capsule endoscope 2 is introduced is written by the image display apparatus 4.

The image display apparatus 4 is an example of the image display apparatus of the present invention and has a configuration of a workstation or the like capable of displaying various information such as an in-vivo image of the subject 1. Concretely, the image display apparatus 4 takes the recording data of the portable recording medium 5, thereby obtaining the series of in-vivo images of the subject 1, the time information of the in-vivo images, and the ID information of the capsule endoscope 2. The image display apparatus 4 determines each of the in-vivo images included in the obtained series of in-vivo images by ID information, and sequentially displays the remaining in-vivo images other than the in-vivo images influenced by fluctuations in the power source voltage out of the series of in-vivo images. The user such as a doctor or nurse visually recognizes the in-vivo images of the subject 1 sequentially displayed on the image display apparatus 4 to observe (examine) a region in the subject 1 such as the esophagus, the stomach, the small intestine, the large intestine, or the like. Based on the observation, the subject 1 can be diagnosed.

Figure 2:
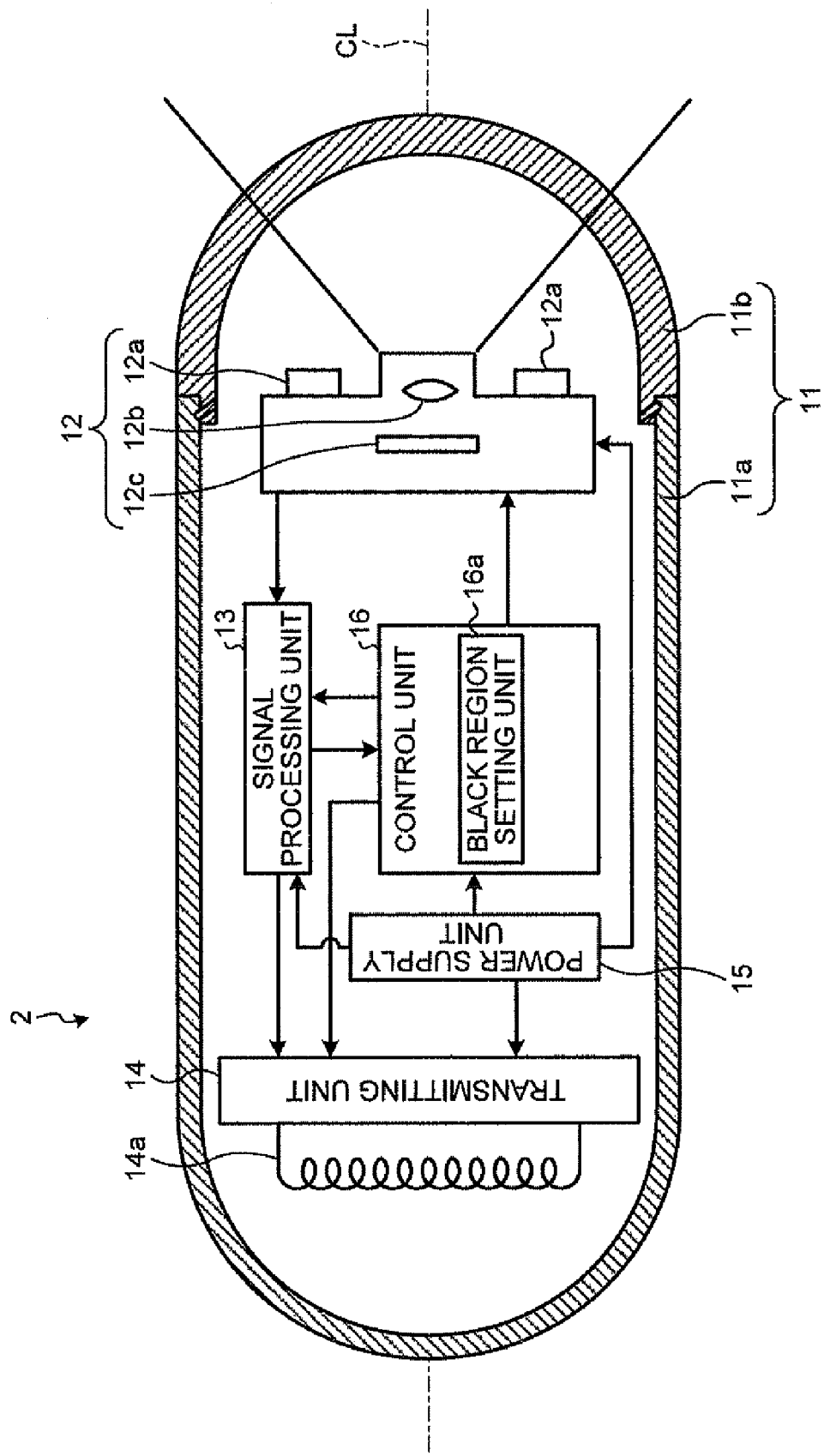
FIG. 2 is a schematic view illustrating a configuration example of a capsule endoscope in the first embodiment of the invention.
Figure 3:
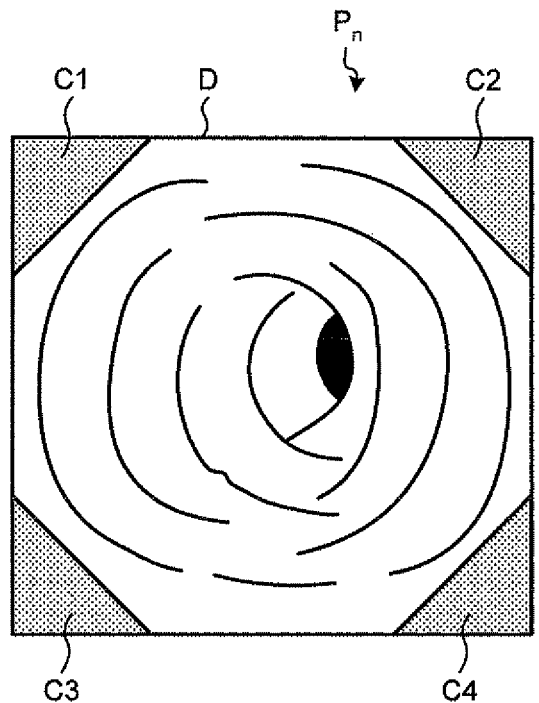
FIG. 3 is a schematic view showing an example of an in-vivo image captured by the capsule endoscope in the first embodiment.

Next, the configuration of the capsule endoscope 2 as an example of the image pickup apparatus in the first embodiment of the present invention will be described in detail. FIG. 2 is a schematic view illustrating a configuration example of the capsule endoscope in the first embodiment of the invention. FIG. 3 is a schematic view showing an example of an in-vivo image captured by the capsule endoscope in the first embodiment. As shown in FIG. 2, the capsule endoscope 2 of the first embodiment has a capsule casing 11 formed by a cylindrical casing 11a and a dome-shaped casing 11b, an imaging unit 12 for capturing an in-vivo image of the subject 1, a signal processing unit 13 for generating an image signal including the in-vivo image captured by the imaging unit 12, and a transmitting unit 14 for wirelessly transmitting the in-vivo image of the subject 1 and the like to the receiving device 3 (refer to FIG. 1) outside the subject 1. The capsule endoscope 2 has a power supply unit 15 realized by a battery or the like and a control unit 16 for controlling the components of the capsule endoscope 2.

The capsule casing 11 is a capsule-shaped casing formed in a size which can be introduced in the subject 1. One end (open end) of the cylindrical casing 11a whose other end has a dome shape is closed with the dome-shaped casing 11b. The dome-shaped casing 11b is an optical dome which is transparent to light having a predetermined wavelength band (for example, visible light). On the other hand, the cylindrical casing 11a is an almost opaque casing. In the capsule casing 11 formed by the cylindrical casing 11a and the dome-shaped casing 11b, the imaging unit 12, the signal processing unit 13, the transmitting unit 14, the power supply unit 15, and the control unit 16 are liquid-tightly housed. In this case, the imaging unit 12 is fixedly disposed so that a center axis CL in the longitudinal direction of the capsule casing and the optical axis almost coincide with each other.

The imaging unit 12 functions as an imaging unit for capturing an in-vivo image of the subject 1, and has an illuminating unit 12a such as an LED, an optical system 12b such as a condenser lens, and a solid-state imaging device 12c such as a CCD or CMOS. A plurality of illuminating units 12a illuminate a subject (concretely, the inside of an organ in the subject 1) over the dome-shaped casing 11b. The optical system 12b condenses reflection light from the subject illuminated by the plurality of illuminating units 12a and forms an optical image of the subject in a light receiving region in the solid-state imaging device 12c.

The solid-state imaging device 12c has a pixel group of an image output region to which an image can be output and a pixel group of an optical black region which is always light-shielded by a film or the like. The solid-state imaging device 12c has, in the image output region, a pixel group of an effective pixel region contributing to imaging and has, in the effective pixel region, a pixel group of a black region where optical rays do not reach. The solid-state imaging device 12c receives reflection light (light information) from the subject condensed by the optical system 12b by the pixel group of the effective pixel region and photo-electrically converting the received light information, thereby obtaining an image of the subject, that is, an in-vivo image of the subject 1. The pixel group of the black region in the solid-state imaging device 12c is off from the light receiving region in the pixel group in the effective pixel region and is optically light-shielded by being set outside of the light receiving region in the solid-state imaging device 12c specified by the optical system 12b.

An in-vivo image $P_n$ (n denotes frame number) of the subject 1 captured by the imaging unit 12 is formed by, for example, as shown in FIG. 3, the pixel group of an effective pixel region D of the solid-state imaging device 12c. In the effective pixel region D, for example, in the four corners of the effective pixel region D, four black regions C1 to C4 where optical rays do not reach as described above are set. Specifically, the signal level of the pixel group forming the in-vivo image Pn includes a signal level of the pixel group contributing to drawing (taking) an in-vivo image of the subject 1 in the pixel group of the effective pixel region D and a signal level of the pixel group of the black regions C1 to C4. The data of the in-vivo image Pn is transmitted from the imaging unit 12 to the signal processing unit 13.

The signal processing unit 13 obtains the data of the in-vivo image Pn captured by the imaging unit 12 and performs a predetermined signal process on the obtained data, thereby generating an image signal including the in-vivo image $P_n$ of the subject 1. The signal processing unit 13 extracts the signal level of each of the pixels in the black regions C1 to C4 (hereinbelow, also simply called "signal level of black region") from the data of the in-vivo image $P_n$. The signal processing unit 13 sequentially transmits the image signals of the in-vivo image $P_n$ (n=1, 2, 3, . . . ) to the transmitting unit 14, and transmits the signal levels of the black regions C1 to C4 to the control unit 16. An image signal generated by the signal processing unit 13 includes not only the data of the in-vivo image $P_n$ but also the ID information of the capsule endoscope 2.

The transmitting unit 14 has a coil-shaped transmitting antenna 14a and transmits a radio signal to the receiving device 3 (refer to FIG. 1) outside of the subject 1 by using the transmitting antenna 14a. Concretely, the transmitting unit 14 obtains an image signal of the in-vivo image Pn from the signal processing unit 13 under control of the control unit 16. Each time the image signal is obtained, the transmitting unit 14 performs a predetermined modulating process or the like on the image signal, generates a radio signal including the in-vivo image $P_n$ and the ID information, and sequentially transmits the generated radio signal to the receiving device 3.

The power supply unit 15 is a built-in power supply in which power to be supplied to the components of the capsule endoscope 2 is stored. Concretely, the power supply unit 15 is realized by using a switch circuit, a button battery, and the like. When the power supply unit 15 is switched to the on state by the switch circuit, power is supplied to the imaging unit 12, the signal processing unit 13, the transmitting unit 14, and the control unit 16.

The control unit 16 controls the components (the imaging unit 12, the signal processing unit 13, the transmitting unit 14, and the like) of the capsule endoscope 2, and controls input/output of a signal among the components. Concretely, the control unit 16 controls the imaging unit 12 to capture an image (that is, an in-vivo image $P_n$) of the subject illuminated by the illuminating unit 12a by the solid-state imaging device 12c. The control unit 16 controls the signal processing unit 13 so as to generate an image signal of the in-vivo image $P_n$ captured by the imaging unit 12. The control unit 16 has a storage unit (not shown) such as a ROM that stores ID information of the capsule endoscope 2 and controls the transmitting unit 14 so as to wirelessly transmit the image signal including the ID information and the in-vivo image $P_n$ to the outside.

The control unit 16 has a black region setting unit 16a for setting the black regions C1 to C4 in the effective pixel region D of the solid-state imaging device 12c. Concretely, the black region setting unit 16a sets a pixel address of the effective pixel region D in an image output region in the solid-state imaging device 12c, and sets pixel addresses of the black regions C1 to C4 in the effective pixel region D which is set. The black region setting unit 16a obtains a signal level (for example, brightness level of each pixel) of each of the black regions C1 to C4 extracted by the signal processing unit 13, and compares the obtained signal level with a predetermined threshold. Based on the result of the comparing process, the black region setting unit 16a determines whether the black regions C1 to C4 are assured in the effective pixel region D or not. When it is determined that the black regions C1 to C4 are assured, the black region setting unit 16a determines the current black regions C1 to C4 as the black regions in the effective pixel region D. On the other hand, in the case where at least one of the black regions C1 to C4 is not assured, the black region setting unit 16a changes each of the pixel addresses in the effective pixel region D in the image output region of the solid-state imaging device 12c (that is, shifts an image reading position in the solid-state imaging device 12c). In such a manner, the black region setting unit 16a adjusts each of the pixel addresses in the black regions C1 to C4 in the effective pixel region D. The black region setting unit 16a repeats the process until all of the black regions C1 to C4 are assured. The control unit 16 controls the imaging unit 12 and the signal processing unit 13 so as to generate an image signal of the in-vivo image $P_n$ including the signal levels of the black regions C1 to C4 set by the black region setting unit 16a.

Figure 4:
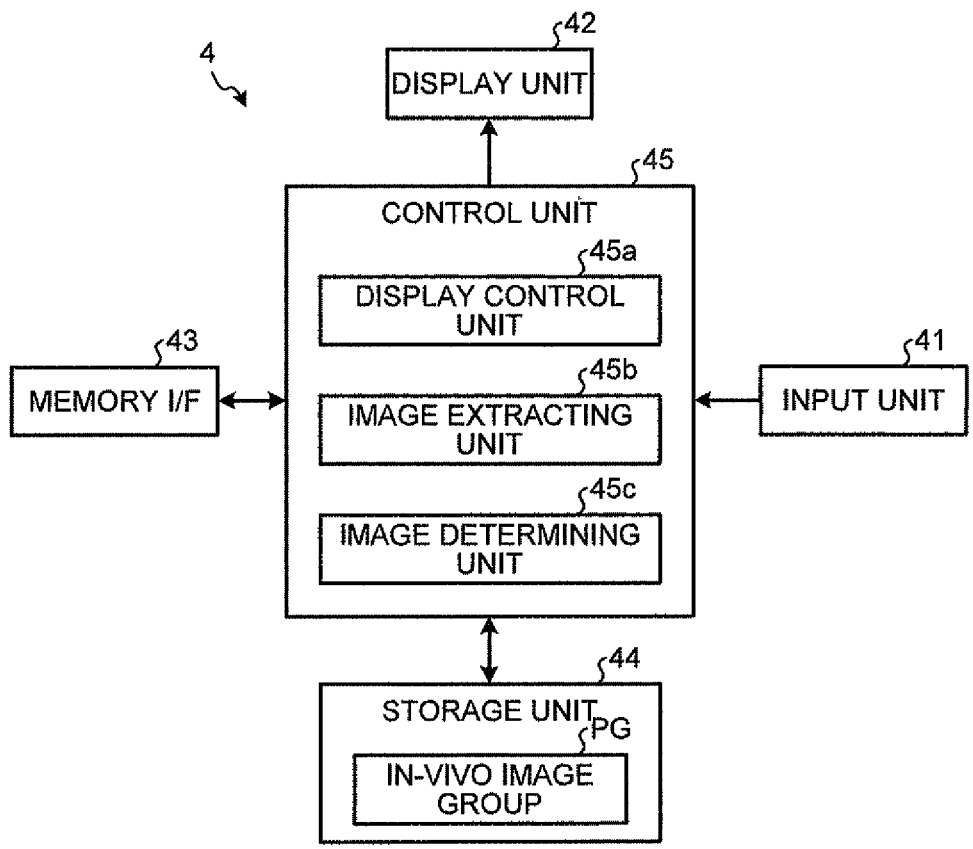
FIG. 4 is a block diagram schematically showing a configuration example of an image display apparatus in the first embodiment of the invention.

Next, the configuration of the image display apparatus 4 in the first embodiment of the present invention will be described. FIG. 4 is a block diagram schematically showing a configuration example of the image display apparatus in the first embodiment of the invention. As shown in FIG. 4, the image display apparatus 4 in the first embodiment has an input unit 41 for inputting various information, a display unit 42 for displaying the in-vivo image $P_n$ of the subject 1, a GUI (Graphical User Interface), and the like on the screen, and a memory interface (I/F) 43 for reading data (a series of in-vivo images of the subject 1 and the like) recorded on the portable recording medium 5. The image display apparatus 4 also includes a storage unit 44 for storing various data such as an in-vivo image group PG as the series of in-vivo images of the subject 1, and a control unit 45 for controlling the components of the image display apparatus 4.

The input unit 41 is realized by using input devices such as a keyboard and a mouse and inputs various information to the control unit 45 according to an input operation of the user. For example, the input unit 41 inputs various instruction information of instructions to the control unit 45, patient information of the subject 1, and the like to the control unit 45. The patient information input by the input unit 41 is, for example, the patient name, sex, birthday, patient ID, and the like of the subject 1.

The display unit 42 is realized by using a display capable of displaying an image such as a CRT display, a liquid crystal display, or the like, and displays various information and the like instructed to be displayed by the control unit 45. Concretely, the display unit 42 displays a GUI related to output (display) of the in-vivo image $P_n$ of the subject 1 and displays the in-vivo image instructed to be output by the control unit 45 from the in-vivo image group PG. In this case, the display unit 42 displays the in-vivo image instructed to be output without displaying an in-vivo image instructed not to be output by the control unit 45 in the in-vivo image group PG. The display unit 42 displays various information related to the present display image of the patient information of the subject 1, image capture time of an in-vivo image, and the like.

The memory I/F 43 functions as image obtaining means for obtaining a series of in-vivo images of the subject 1 captured by the capsule endoscope 2. Concretely, in the memory I/F 43, the portable recording medium 5 is detachably inserted. The memory I/F 43 obtains the data recorded on the portable recording medium 5, that is, the series of in-vivo images of the subject 1, the ID information of the capsule endoscope 2, and the like. The memory I/F 43 transfers the recorded data taken from the portable recording medium 5 to the control unit 45. The memory I/F 43 writes information instructed to be written by the control unit 45, for example, the patient information or the like of the subject 1 onto the inserted portable recording medium 5.

The storage unit 44 is realized by using a recording medium of a large capacity such as a RAM, an EEPROM, or a hard disk. The storage unit 44 stores various data instructed to be stored by the control unit 45, and transmits the stored data instructed to be read by the control unit 45 to the control unit 45. The storage unit 44 stores the in-vivo image group PG as a series of in-vivo images of the subject 1 read from the portable recording medium 5 by the memory I/F 43. In this case, each of the in-vivo images $P_n$ of the in-vivo image group PG stored in the storage unit 44 is associated with ID information of the capsule endoscope 2 capturing the in-vivo image group PG, time information such as imaging time, reception time, or the like, the patient information of the subject 1 and the like.

The control unit 45 controls the components (the input unit 41, display unit 42, memory I/F 43, storage unit 44, and the like) of the image display apparatus 4 and controls input/output of signals among the components. Concretely, the control unit 45 controls the operations of the display unit 42, the memory I/F 43, and the storage unit 44 based on the instruction information input by the input unit 41. The control unit 45 controls the memory I/F 43, obtains the series of in-vivo images of the subject 1, the ID information of the capsule endoscope 2, and the time information such as imaging time, and associates the in-vivo images included in the obtained series of in-vivo images, the ID information of the capsule endoscope 2, the time information of the in-vivo images, and patient information of the subject 1 with each other. The control unit 45 stores the in-vivo image group PG including the in-vivo images $P_n$ associated with the ID information, the time information, and the like into the storage unit 44.

The control unit 45 has a display control unit 45a, an image extracting unit 45b, and an image determining unit 45c. The display control unit 45a displays various information such as the in-vivo image $P_n$ of the subject 1 on the display unit 42 based on the instruction information input by the input unit 41. In this case, the display control unit 45a displays the in-vivo images other than the in-vivo image inhibited to be output by the image determining unit 45c in the in-vivo image group PG of the subject 1, that is, the in-vivo image permitted to be output by the image determining unit 45c on the display unit 42.

The image extracting unit 45b extracts a series of images including an in-vivo image to be subjected to the image determining process of the image determining unit 45c, which are a group of successive images which continue only by a predetermined number of frames in time series from the in-vivo image group PG of the subject 1. The successive image group extracted by the image extracting unit 45b may be a successive image group including, in the head frame, the in-vivo image to be subjected to the image determining process, a successive image group in which predetermined number of frames of the in-vivo images are successive before and after the in-vivo image to be subjected to the image determining process, or a successive image group including, in the last frame, an in-vivo image to be subjected to the image determining process. The image extracting unit 45b sequentially extracts the successive image group every in-vivo image included in the in-vivo image group PG.

The image determining unit 45c performs the image determining process for determining an in-vivo image with respect to the influence on the image caused by output fluctuations (voltage fluctuations) of the power supply unit 15 of the capsule endoscope 2, for example, the influence on the image caused by fluctuations in the black reference level. Concretely, the image determining unit 45c calculates the number of 0-level pixels in the black regions C1 to C4 based on the signal levels of the black regions C1 to C4 in the in-vivo image in the successive image group extracted by the image extracting unit 45b from the in-vivo image group PG. The image determining unit 45c performs the image determining process on the in-vivo image by using the calculated 0-level pixel number, and inhibits output of an in-vivo image determined by the image determining process that the image is influenced by fluctuations in the power source voltage. The number of 0-level pixels is the number of pixels (the number of pixels of low brightness level) in the black regions C1 to C4 having a brightness level lower than a normal signal level (for example, normal brightness level) of the black regions C1 to C4 output from the imaging unit 12 in the case where there is no fluctuation in outputs of the power supply unit 15 in the capsule endoscope 2 shown in FIG. 2. The number of 0-level pixels is an example of pixel information in the black region which changes with fluctuations in the output of the power supply unit 15 for supplying power to the imaging unit 12. The 0-level pixel number is zero in a state where the fluctuations in the output of the power supply unit 15 in the beginning or the like of the operation of the capsule endoscope 2. The 0-level pixel number increases as the fluctuations in the output of the power supply unit 15 increase, that is, as the power of the power supply unit 15 is consumed. The image determining unit 45c sequentially performs the image determining process on the in-vivo images $P_n$ (n=1, 2, 3, . . . ) by comparing the pixel information (for example, an average value of the 0-level pixel numbers) of the black regions C1 to C4 with a predetermined threshold which is preliminarily set. The image determining unit 45c inhibits output of an in-vivo image which is determined as an image influenced by fluctuations in the power source voltage by the image determining process, and permits output of an in-vivo image which is determined as a stable image that is not influenced by fluctuations in the output of the power source voltage.

In the case where a plurality of in-vivo image groups captured by a plurality of capsule endoscopes 2 of different ID information are stored in the storage unit 44, the image determining unit 45c performs the image determining process on the in-vivo images by the ID information of the capsule endoscopes 2.

Figure 5:
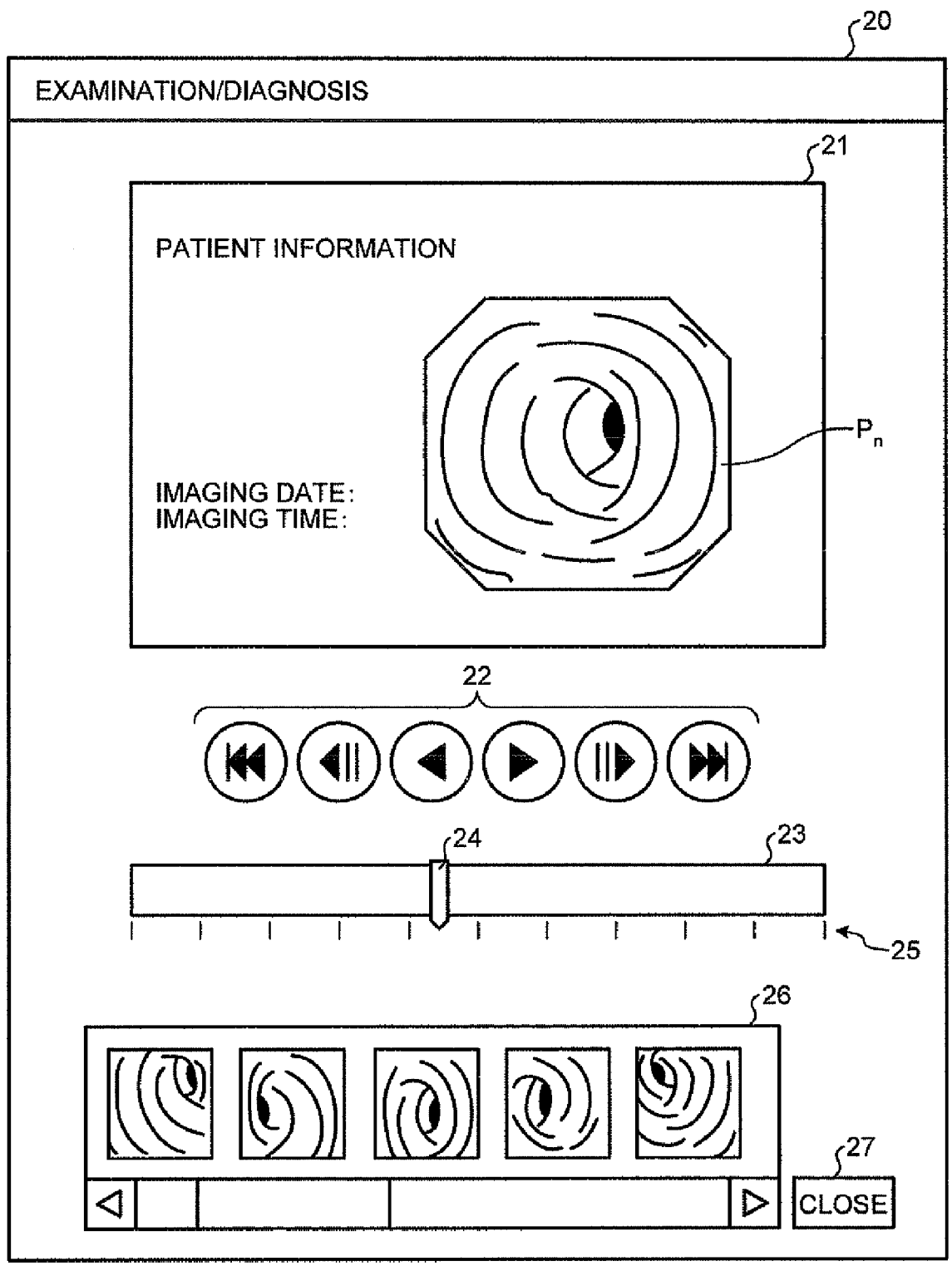
FIG. 5 is a schematic view showing a concrete example of a display mode of a display unit for displaying an in-vivo image.

Next, the display mode of the display unit 42 at the time of displaying the in-vivo image Pn of the subject 1 will be described. FIG. 5 is a schematic view showing a concrete example of the display mode of the display unit for displaying an in-vivo image. When a predetermined log-in process is performed by the control unit 45, the display control unit 45a of the image display apparatus 4 displays a window 20 on which an image of the subject 1 as shown in FIG. 5 is observed on the display unit 42.

As shown in FIG. 5, in the window 20, a main display region 21, a display operation icon group 22, a bar 23, a slider 24, a sub-display region 26 and a "close" icon 27 are formed.

In the main display region 21, the in-vivo image Pn or the like is displayed. The display operation icon group 22 is provided for performing various display operations at the time of displaying the in-vivo image Pn in the main display region 21. With the bar 23, a position in time of the image (in-vivo image Pn) displayed in the main display region 21 or an image number in all of images displayed is indicated. The slider 24 slides along the bar 23 corresponding to the image displayed in the main display region 21. In the sub-display region 26, desired size-reduced in-vivo images selected from the in-vivo image group PG displayed in the main display region 21 are displayed. The "close" icon 27 is used to close the window 20.

The display control unit 45a displays the in-vivo image Pn (specifically, an in-vivo image permitted to be output by the image determining unit 45c) of the subject 1 in the main display region 21 based on the instruction information entered by the input unit 41 in accordance with a display operation icon included in the display operation icon group 22. In this case, the display unit 42 displays image pickup year/month/date and time of the in-vivo image Pn and the patient information of the subject 1 on the main display region 21.

The bar 23 is provided with a time scale 25 indicative of time length (for example, time elapsed since start of image capture) of an in-vivo image group to be displayed which is permitted to be output by the image determining unit 45c among the in-vivo image groups PG of the subject 1. By the time scale 25, a position with respect to time of each of the in-vivo images in the in-vivo image group to be displayed is indicated. The length (width) of the bar 23 indicative of the position in time of the in-vivo image group to be displayed is controlled by the display control unit 45a.

The slider 24 moves along the bar 23 and indicate the position in time on the bar 23 corresponding to the present display image in the main display region 21. The movement of the slider 24 is controlled by the display control unit 45a. That is, the display control unit 45a controls movement of the slider 24 on the bar 23 and display switch of the present display image in the main display region 21 so that the slider 24 always shows the position in time of the presently displayed image (in-vivo image Pn of the subject 1) in the main display region 21.

Figure 6:
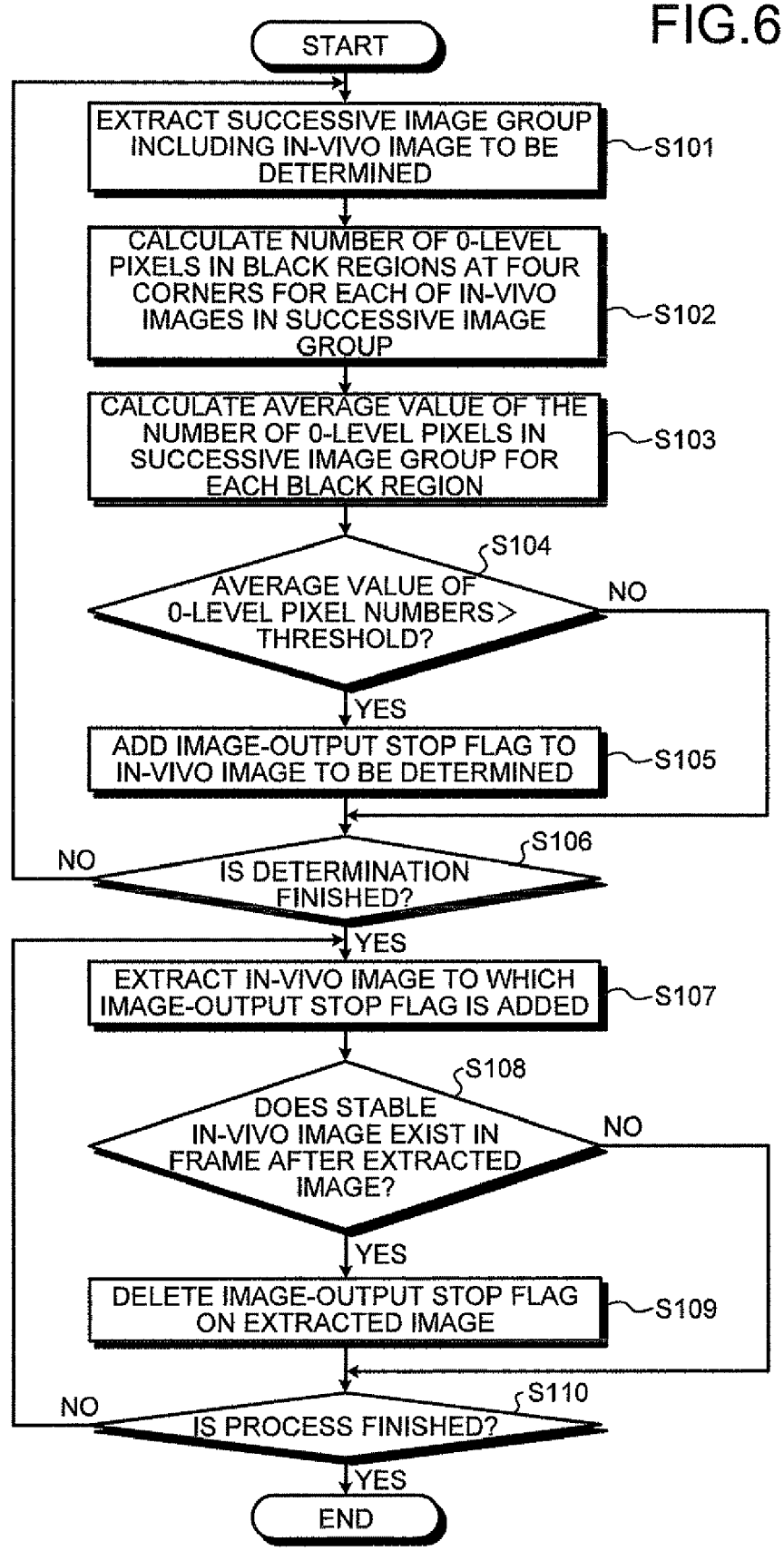
FIG. 6 is a flowchart showing a procedure of a control unit in an image display apparatus for performing an image determining process on an in-vivo image by using the number of pixels of level 0 in a black region.

Next, the operation of the image display apparatus 4 in the first embodiment of the present invention will be described. FIG. 6 is a flowchart illustrating a procedure of a control unit in an image display apparatus for performing the image determining process on an in-vivo image by using the 0-level pixel number in a black region. In the case where the in-vivo image group PG of the subject 1 is taken from the portable recording medium 5 inserted in the memory I/F 43, the control unit 45 in the image display apparatus 4 performs the image determining process on each of the in-vivo images Pn (n=1, 2, 3, . . . ) in the in-vivo image group PG with respect to the influence on an image caused by consumption of the power of the power supply unit 15 of the capsule endoscope 2. According to a result of the image determining process, the control unit 45 inhibits or permits output of the in-vivo image Pn.

As shown in FIG. 6, the control unit 45 extracts a successive image group including an in-vivo image Pn to be subjected to the image determination from the in-vivo image group PG of the subject 1 taken from the portable recording medium 5 inserted in the memory I/F 43 (step S801). In this case, the image determining unit 45c determines the in-vivo image Pn to be subjected to the image determining process (hereinbelow, also simply called in-vivo image to be determined) from the in-vivo image group PG along the forward direction of the time series (the ascending order of frame numbers "n"). The image extracting unit 45b extracts a successive image group of predetermined frames (for example, three frames) including the in-vivo image Pn to be determined by the image determining unit 45c.

Next, the control unit 45 calculates the number of 0-level pixels of the black regions C1 to C4 at four corners in each of the in-vivo images in the successive image group extracted in step S101 (step S102). In this case, the image determining unit 45c obtains the signal level (for example, brightness level) of each of the pixels of the black regions C1 to C4 in each of the in-vivo images included in the successive image group, and compares the obtained signal level of each pixel with a predetermined threshold. The image determining unit 45c uses, as the threshold, for example, the signal level of the black region when consumption of the power of the power supply unit 15 in the capsule endoscope 2 is small. The image determining unit 45c calculates the number of pixels having a signal level lower than the threshold with respect to each of the pixel groups of the black regions C1 to C4 and, as a result, obtains the 0-level pixel number of each of the black regions C1 to C4. The image determining unit 45c repeats the computing process on the in-vivo image unit basis, thereby calculating the 0-level pixel number of each of the black regions C1 to C4 for each of the in-vivo images in the successive image group.

Subsequently, based on each of the 0-level pixel numbers in the black regions C1 to C4 calculated for each of the in-vivo images in step S102, the control unit 45 calculates an average value of the 0-level pixel number in the successive image group on each of the black regions (step S103). In this case, the image determining unit 45c divides the total value of the 0-level pixel numbers in the black region C1 in each of the in-vivo images in the successive image group by the number of frames in the successive image group, and calculates the average value of the 0-level pixel numbers in the black region C1 in the successive image group. Similarly, the image determining unit 45c divides the total value of the 0-level pixel numbers in the black region C2 in the successive image group by the number of frames in the successive image group, and calculates the average value of the 0-level pixel numbers in the black region C2 in the successive image group. The image determining unit 45c divides the total value of the 0-level pixel numbers in the black region C3 in the successive image group by the number of frames in the successive image group, and calculates the average value of the 0-level pixel numbers in the black region C3 in the successive image group. The image determining unit 45c divides the total value of the 0-level pixel numbers in the black region C4 in the successive image group by the number of frames in the successive image group, and calculates the average value of the 0-level pixel numbers in the black region C4 in the successive image group.

Next, the control unit 45 determines whether the average value of the 0-level pixel numbers in each of the black regions C1 to C4 calculated in step S103 exceeds a predetermined threshold or not (step S104). In the case where the average value exceeds the predetermined threshold (Yes in step S104), it is determined that the in-vivo image Pn to be determined is influenced by fluctuations in the power source voltage, and an image output stop flag is added to the in-vivo image Pn to be determined (step S105). In steps S104 and S105, the image determining unit 45c compares the average value of the 0-level pixel numbers in each of the black regions C1 to C4 with the preset threshold. In the case where the average value of each of the 0-level pixel numbers exceeds the threshold, the image determining unit 45c determines that the in-vivo image Pn to be determined in the step S101 is influenced by fluctuations in the power source voltage, and adds an image output stop flag to the in-vivo image to be determined. The image output stop flag is a mark indicating that output of an image to the display unit 42 is to be stopped. By adding the image output stop flag to an in-vivo image, the image determining unit 45c inhibits output of the in-vivo image determined as an image influenced by fluctuations in the power source voltage (that is, display output to the display unit 42).

After that, the control unit 45 determines whether or not the determination on all of in-vivo images included in the in-vivo image group PG of the subject 1 has been finished (step S106). If the determination has not been finished (No in step S106), the control unit 45 returns to step S101 and repeats the processes of the step S101 and the subsequent steps. If the in-vivo image to be determined is not the last in-vivo image in the in-vivo image group PG, in step S106, the image determining unit 45c determines that the determination on all of the in-vivo images in the in-vivo image group PG has not been finished.

In the case where the average value of the 0-level pixel numbers in each of the black regions C1 to C4 is equal to or less than the predetermined threshold in the step S104 (No in step S104), the control unit 45 determines that the in-vivo image Pn to be determined is a stable image which is not influenced by fluctuations in the power source voltage. Without adding the image output stop flag to the in-vivo image Pn to be determined, the control unit 45 advances to step S106. In this case, the image determining unit 45c compares the average value of the 0-level pixel numbers of the black regions C1 to C4 with the preset threshold. In the case where the average value of the 0-level pixel numbers is equal to or less than the threshold value, the in-vivo image Pn to be determined is determined as a stable image which is not influenced by fluctuations in the power source voltage. Without adding the image output stop flag to a stable in-vivo image which is not influenced by fluctuations in the power source voltage, the image determining unit 45c permits output of the stable in-vivo image which is not influenced by fluctuations in the power source voltage.

On the other hand, in the case where it is determined that determination of all of in-vivo images in the in-vivo image group PG in the step S106 is finished (Yes in step S106), the control unit 45 extracts an in-vivo image determined as an image influenced by fluctuations in the power source voltage from the in-vivo image group PG. In this case, the image extracting unit 45b extracts an in-vivo image to which the image output stop flag is added from the in-vivo image group PG subjected to the image determination by the processes in the steps S101 to S106 (step S107).

Next, the control unit 45 determines whether or not a stable in-vivo image which is not influenced by fluctuations in the power source voltage exists in a frame after one or more images extracted from the in-vivo image group PG in step S107 (that is, the in-vivo image determined as an image influenced by fluctuations in the power source voltage) (step S108). In the case where a stable in-vivo image which is not influenced by fluctuations in the power source voltage exists (Yes in step S108), the image output stop flag of the extracted image is deleted (step S109). In steps S108 and S109, the image determining unit 45c sequentially pays attention to the one or more extracted images, that is, the in-vivo images to which the image output stop flag is added (that is, determined as images influenced by fluctuations in the power source voltage) in ascending order of the frame numbers "n". In the case where an in-vivo image to which the image output stop flag is not added (a stable in-vivo image which is not influenced by fluctuations in the power source voltage) exists in a frame after the in-vivo image (the in-vivo image determined as an image influenced by fluctuations in the power source voltage) to which attention is paid, the image determining unit 45c deletes the image output stop flag of the in-vivo image to which attention is paid, thereby cancelling the inhibition of output of the in-vivo image.

On the other hand, in the case where it is determined in the step S108 that a stable in-vivo image which is not influenced by fluctuations in the power source voltage does not exist in frames after the one or more extracted image (No in step S108), the control unit 45 does not delete the image output stop flag of the extracted image. In this case, the image determining unit 45c confirms that an in-vivo image to which the image output stop flag is not added (a stable in-vivo image which is not influenced by fluctuations in the power source voltage) does not exist in frames after the extracted image (the in-vivo image determined as an image influenced by fluctuations in the power source voltage) to which attention is paid in the step S108. Based on the fact, the image output stop flag of the in-vivo image to which attention is paid is not deleted, and a state where the image output stop flag is added to the image is maintained. As a result, the image determining unit 45c maintains inhibition of output of the in-vivo image to which attention is paid.

After that, the control unit 45 determines whether or not the process has been finished on all of in-vivo images determined as images influenced by fluctuations in the power source voltage in the in-vivo image group PG (step S110). If the process has not been finished (No in step S110), the control unit 45 returns to the step S107 and repeats the processes in the step S107 and subsequent steps. In the step S110, when the in-vivo image to which attention is paid is not the last one of the in-vivo images determined as images influenced by fluctuations in the power source voltage, the image determining unit 45c determines that the process has not been finished. On the other hand, when the in-vivo image to which attention is paid is the last one of the in-vivo images determined as images influenced by fluctuations in the power source voltage, the image determining unit 45c determines that the process has been finished (Yes in step S110) and the control unit 45 finishes the process.

By repeatedly performing the processes in the steps S101 to S106, the control unit 45 achieves the image determining process (the image determining process in the first stage performed by the image determining unit 45c) on each of the in-vivo images Pn using the 0-level pixel numbers of the black regions C1 to C4. Further, by repeatedly performing the processes in the steps S107 to S110, the image determining process for determining whether or not an in-vivo image determined as an image influenced by fluctuations in the power source voltage is really an in-vivo image influenced by fluctuations in the power source voltage (the image determining process in the second stage performed by the image determining unit 45c) can be achieved. By performing the image determining process in two stages, the image determining unit 45c can reliably stop outputting the in-vivo image influenced by fluctuations in the power source voltage and whose quality is deteriorated by the fluctuations in output of the power source. In addition, inhibition of output of an in-vivo image slightly influenced by fluctuations in the power source voltage, in the in-vivo images determined as images influenced by fluctuations in the power source voltage can be cancelled. As a result, without displaying the in-vivo image influenced by fluctuations in the power source voltage on the display unit 42, the remaining in-vivo images except for the in-vivo image influenced by fluctuations in the power source voltage in the in-vivo image group PG, that is, larger number of stable in-vivo images can be displayed on the display unit 42 and provided to the user.

Figure 7:
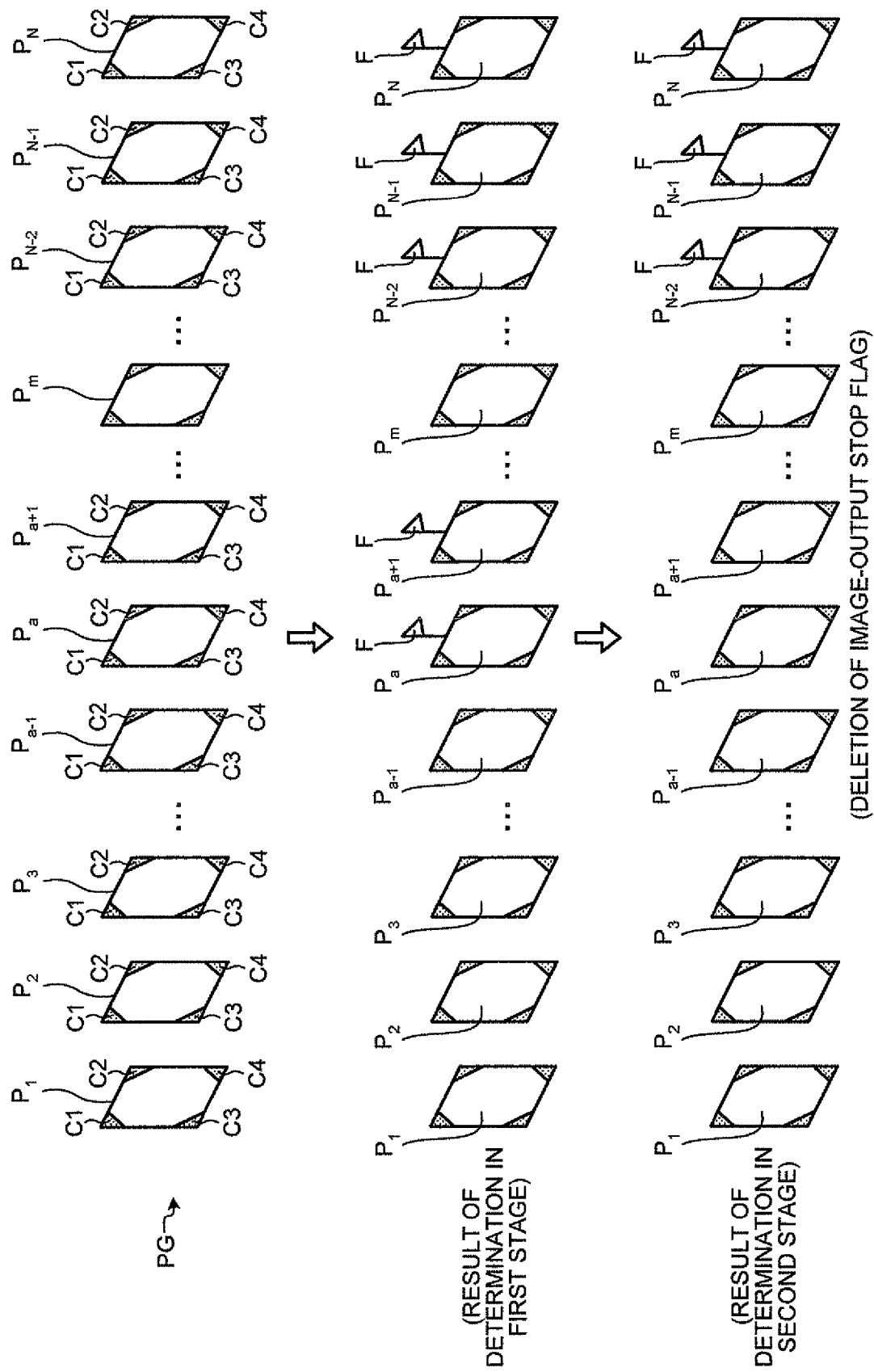
FIG. 7 is a schematic view for explaining the image determining process in two stages performed by an image determining unit of the image display apparatus of the first embodiment.

Next, the case of extracting a group of three successive images (three frames) including an in-vivo image to be determined from the in-vivo image group PG made of N in-vivo images Pn (n=1, 2, 3, ..., N) will be described as an example, and the image determining process in two stages on the in-vivo images Pn will be concretely described. FIG. 7 is a schematic view for explaining the image determining process in two stages performed by the image determining unit in the image display apparatus of the first embodiment.

In FIG. 7, an in-vivo image $P_a$ (1<a<N) in the a-th frame is an object of determination of the image determining unit 45c. A successive image group of the in-vivo image $P_a$ to be determined and immediately preceding and subsequent frame of in-vivo images $P_{a-1}$ and $P_{a+1}$ is an image group extracted from the in-vivo image group PG by the image extracting unit 45b at the time of performing the image determining process on the in-vivo image Pa. In this case, the image determining unit 45c calculates an average value of the 0-level pixel numbers of the black regions C1 to C4 in the in-vivo images $P_{a-1}$, $P_a$, and $P_{a+1}$, and performs the image determining process in the first stage on the in-vivo image $P_a$ to be determined by using the calculated average value.

Concretely, the image determining unit 45c sequentially calculates the 0-level pixel number in each of the black regions C1 to C4 in the in-vivo image $P_{a-1}$, the 0-level pixel number in each of the black regions C1 to C4 in the in-vivo image $P_a$, and the 0-level pixel number in each of the black regions C1 to C4 in the in-vivo image $P_{a+1}$. The image determining unit 45c calculates an average value K1 of the 0-level pixel numbers in the black regions C1 in the in-vivo images $P_{a-1}$, $P_a$, and $P_{a+1}$ by dividing the total value of the 0-level pixel numbers in the black regions C1 in the in-vivo images $P_{a-1}$, $P_a$, and $P_{a+1}$ by the number of frames "3" in the successive image group. Similarly, the image determining unit 45c calculates an average value K2 of the 0-level pixel numbers in the black regions C2 in the in-vivo images $P_{a-1}$, $P_a$, and $P_{a+1}$ by dividing the total value of the 0-level pixel numbers in the black regions C2 in the in-vivo images $P_{a-1}$, $P_a$, and $P_{a+1}$ by the number of frames "3" in the successive image group. The image determining unit 45c calculates an average value K3 of the 0-level pixel numbers in the black regions C3 in the in-vivo images $P_{a-1}$, $P_a$, and $P_{a+1}$ by dividing the total value of the 0-level pixel numbers in the black regions C3 in the in-vivo images $P_{a-1}$, $P_a$, and $P_{a+1}$ by the number of frames "3" in the successive image group. The image determining unit 45c calculates an average value K4 of the 0-level pixel numbers in the black regions C4 in the in-vivo images $P_{a-1}$, $P_a$, and $P_{a+1}$ by dividing the total value of the 0-level pixel numbers in the black regions C4 in the in-vivo images $P_{a-1}$, $P_a$, and $P_{a+1}$ by the number of frames "3" in the successive image group.

The image determining unit 45c compares the average values K1 to K4 of the 0-level pixel numbers in the black regions C1 to C4 calculated as described above with the preset threshold. In the case where at least one of the average values K1 to K4 exceeds the threshold, the image determining unit 45c determines that the in-vivo image $P_a$ to be determined is influenced by fluctuations in the power source voltage. In the case where all of the average values K1 to K4 are equal to or less than the threshold, the image determining unit 45c determines that the in-vivo image $P_a$ to be determined as a stable image which is not influenced by fluctuations in the power source. In the case where the in-vivo image $P_a$ to be determined is determined as an image influenced by fluctuations in the power source voltage, the image determining unit 45c adds the image output stop flag F to the in-vivo image $P_a$ determined as an image influenced by fluctuations in the power source voltage.

In a manner similar to the case of the in-vivo image $P_a$, the image determining unit 45c repeatedly performs the image determining process in the first stage on each of the in-vivo images Pn (n=1, 2, 3, ..., N) in the in-vivo image group PG. To all of in-vivo images determined as images influenced by fluctuations in the power source voltage by the image determining process in the first stage, an image output stop flag F is added.

In the case where the image determining unit 45c performs the image determining process on the in-vivo image $P_1$ in the first frame, the image extracting unit 45b may extract a successive image group of the in-vivo image $P_1$ to be determined and two frames of in-vivo images $P_3$ and $P_3$ subsequent to the in-vivo image $P_1$. In the case where the image determining unit 45c performs the image determining process on the in-vivo image $P_N$ in the N-th frame, the image extracting unit 45b may extract a successive image group of the in-vivo image $P_N$ to be determined and two frames of in-vivo images $P_{N-2}$ and $P_{N-1}$ before the in-vivo image $P_N$.

As described above, in the case where the image determining process in the first stage to each of the in-vivo images Pn in the in-vivo image group PG is finished, the image determining unit 45c performs the image determining process in the second stage on an in-vivo image determined as an image influenced by fluctuation in the power source voltage in the in-vivo image group PG. Concretely, the image determining unit 45c pays attention to an in-vivo image of the smallest frame number (the in-vivo image $P_a$ in FIG. 7) in in-vivo images determined as images influenced by fluctuations in the power source voltage extracted by the image extracting unit 45b from the in-vivo image group PG. The image determining unit 45c determines whether or not a stable in-vivo image which is not influenced by fluctuations in the threshold power source voltage exists in a frame of the in-vivo image $P_a$ to which attention is paid and subsequent frames.

As shown in FIG. 7, in the case where a stable in-vivo image $P_m$ (a<m<N) to which the image output stop flag F is not added exists in a frame after the in-vivo image $P_a$, even if the image output stop flag F is added to the subsequent in-vivo image $P_{a+1}$, the image determining unit 45c deletes the image output stop flag F of the in-vivo image $P_a$ to which attention is paid, thereby cancelling the inhibition of output of the in-vivo image $P_a$ (that is, permitting output of the image). The image determining unit 45c similarly performs the image determining process in the second stage on the rest of in-vivo images determined as images influenced by fluctuations in the power source voltage. As a result, the image output stop flags F on all of in-vivo images determined as images influenced by fluctuations in the power source voltage existing in frames before the in-vivo image to which the image output stop flag F is not added (stable in-vivo image which is not influenced by fluctuations in the power source voltage) are deleted. On the other hand, as illustrated by the in-vivo images $P_{N-2}$, $P_{N-1}$, and $P_N$ in FIG. 7, in the case where a stable in-vivo image which is not influenced by fluctuations in the power source voltage does not exist in a frame after the in-vivo image determined as an image influenced by fluctuations in the power source voltage, the image determining unit 45c does not delete the image output stop flag F on the in-vivo image determined as an image influenced by fluctuations in the power source voltage (in FIG. 7, the in-vivo images $P_{N-2}$, $P_{N-1}$, and $P_N$). Therefore, the inhibition of output of the in-vivo images is maintained. In such a manner, the image determining unit 45c achieves the image determining process in the second stage on the in-vivo images $P_n$ in the in-vivo image group PG.

The in-vivo images to which the image output stop flag F is finally added by the image determining process in the second stage by the image determining unit 45c (the in-vivo images $P_{N-2}$, $P_{N-1}$, and $P_N$ in FIG. 7) are excluded from images to be displayed on the display unit 42. That is, the display control unit 45a displays, on the display unit 42, the in-vivo images other than the in-vivo images $P_{N-2}$, $P_{N-1}$, and $P_N$ determined as images influenced by fluctuations in the power source voltage in the in-vivo image group PG of the subject 1, that is, stable in-vivo images which are finally permitted to be output by the image determining unit 45c and are not influenced by fluctuations in the power source voltage.

Figure 8:
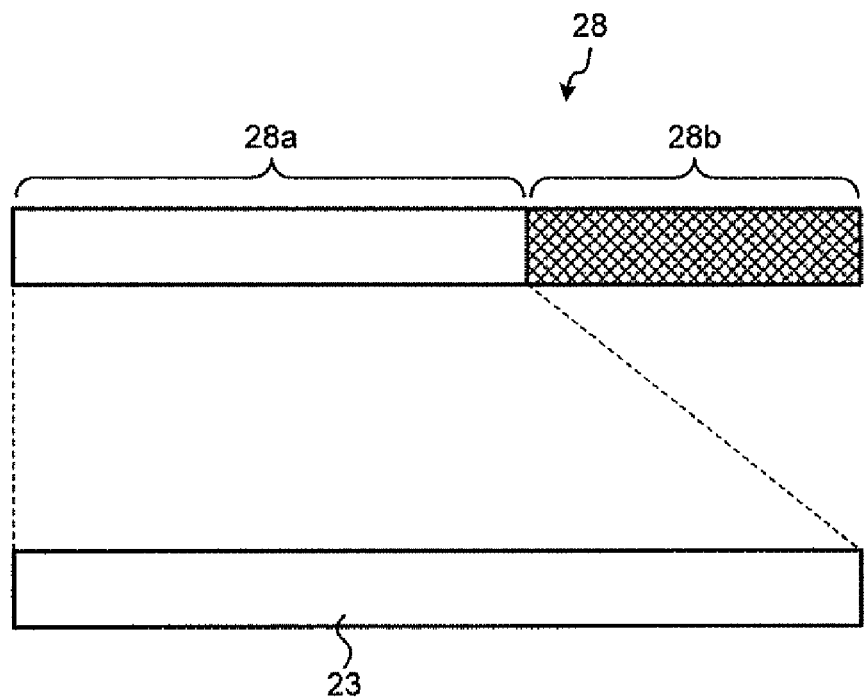
FIG. 8 is a schematic view for explaining the display mode of a time bar indicative of a temporal position in each of an in-vivo image finally permitted to be output by the image determining unit.

Next, the display mode of the bar 23 (refer to FIG. 5) showing a temporal position of each of the in-vivo images finally permitted to be output by the image determining unit 45c will be described. FIG. 8 is a schematic diagram for explaining the display mode of the bar indicative of a temporal position of each of the in-vivo images finally permitted to be output by the image determining unit.

The display unit 42 of the image display apparatus 4 in the first embodiment displays the bar 23 as shown in FIG. 5. The bar 23 indicates the temporal position of an in-vivo image displayed in the main display region 21 of the display unit 42, that is, an in-vivo image finally permitted to be output by the image determining unit 45c.

In the case where all of in-vivo images included in the in-vivo image group PG of the subject 1 are permitted to be output, the display control unit 45a displays a bar indicating a temporal position of all of the in-vivo images or an image number in all of the display numbers (hereinbelow, called basic bar) on the display unit 42. On the other hand, in the case where one or more in-vivo image finally inhibited to be output by the image determining unit 45c is included in the in-vivo image group PG, the display control unit 45a displays, on the display unit 42, a bar (the bar 23 shown in FIG. 5) indicating a temporal position of each of the in-vivo images other than one or more in-vivo images inhibited to be output, that is, each of the in-vivo images finally permitted to be output by the image determining unit 45c.

Concretely, as shown in FIG. 8, the display control unit 45a excludes the part indicative of the position of the in-vivo image inhibited to be output or indicative of an image number in all of the display numbers in the basic bar 28, that is, a partial bar 28b from the object of display of the display unit 42, and displays the rest partial bar 28a on the display unit 42. The partial bar 28a is a part indicative of the positions of the in-vivo images finally permitted to be output in the basic bar 28. The display control unit 45a displays, as the bar 23, a bar obtained by enlarging the length in the time axis direction of the partial bar 28a to a length to that of the basic bar 28 on the display unit 42. The bar 23 whose display mode is adjusted by the display control unit 45a has a scale similar to that of the partial bar 28a.

By displaying the bar 23 whose display mode is adjusted on the display unit 42, an in-vivo image displayed in the display unit 42 and the temporal position indicated by the bar 23 can be correlated, and display operability when the user such as a doctor or nurse observes an in-vivo image can be improved.

Figure 9:
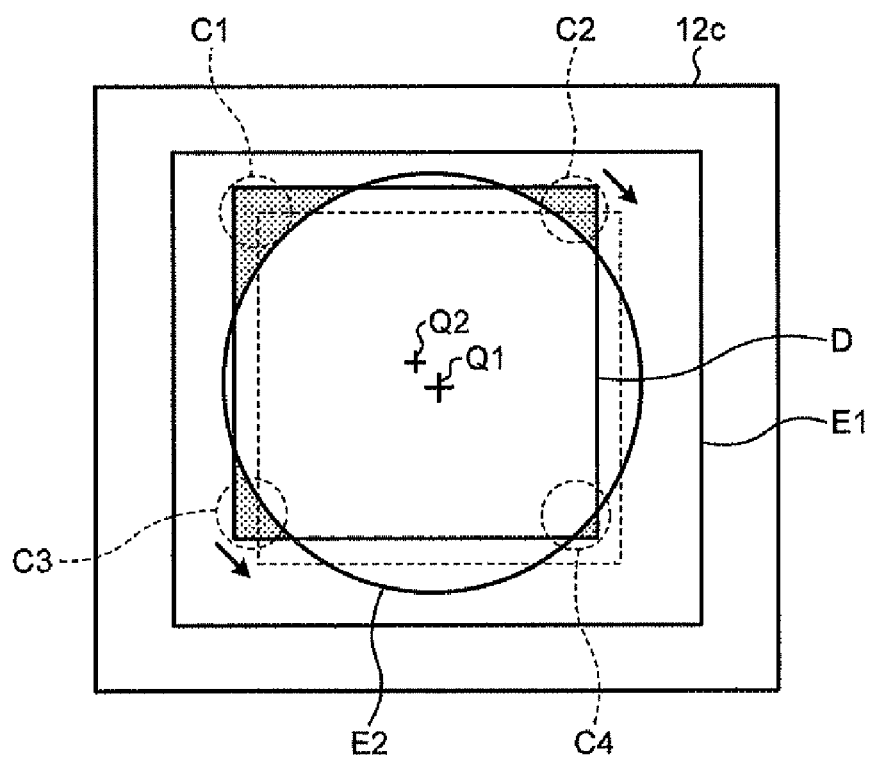
FIG. 9 is a schematic view for explaining operation of a black region setting unit for adjusting a black region in an effective pixel region.

Next, the operation of the black region setting unit 16a for adjusting the black regions C1 to C4 of the solid-state imaging device 12c will be described. FIG. 9 is a schematic diagram for explaining the operations of the black region setting unit for adjusting a black region in an effective pixel region.

FIG. 9 schematically shows the solid-state imaging device 12c viewed from the pixel group side in the image output region.

As described above, the black region setting unit 16a (refer to FIG. 2) in the capsule endoscope 2 as an example of the image pickup apparatus in the first embodiment of the invention obtains the signal level (for example, the brightness level of each pixel) of each of the black regions C1 to C4 extracted by the signal processing unit 13. Based on the obtained signal levels, the black region setting unit 16a determines whether or not the black regions C1 to C4 are assured in the effective pixel region D in the solid-state imaging device 12c. Concretely, the black region setting unit 16a compares the signal levels of the black regions C1 to C4 with a preset threshold. In the case where at least one of the signal levels exceeds the preset threshold, the black region setting unit 16a determines that at least one of the black regions C1 to C4 is not assured. In the case where all of the signal levels are equal to or less than the preset threshold, the black region setting unit 16a determines that the black regions C1 to C4 are assured.

An example of the causes of a situation that at least one of the black regions C1 to C4 is not assured in the effective pixel region D in the solid-state imaging device 12c is that the center of image capture of the imaging unit 12 and the light reception center are deviated from each other due to an assembly error of the imaging unit 12 or the like.

As shown in FIG. 9, in the case where the black region C4 at the right lower corner as one of the black regions C1 to C4 at the four corners of the solid-state imaging device 12c is not assured, the signal level of the black region C4 exceeds the preset threshold. Based on the fact, the black region setting unit 16a determines that the black region C4 is not assured, and adjusts the pixel address in the black region C4. In this case, the black region setting unit 16a adjusts (changes) each of the pixel addresses of the effective pixel region D to the black region C4 side (lower right side in FIG. 9) in an image output region E1 in the solid-state imaging device 12c. In such a manner, the effective pixel region D is shifted so that a light reception center Q1 as the center of a light receiving region E2 and an image capture center Q2 as a center of the effective pixel region D coincide with each other. As a result, the black region C4 where optical rays do not reach is assured at the right lower corner of the effective pixel region D.

The light receiving region E2 is a pixel region for receiving light entering via the optical system 12b in the image output region E1, and is specified by the optical system 12b. The light reception center Q1 as a center of the light receiving region E2 is positioned on the optical axis of the optical system 12b.

The black region setting unit 16a compares each of the signal levels of the adjusted black regions C1 to C4 with the preset threshold. In the case where at least one of the signal levels exceeds the preset threshold, the black region setting unit 16a re-adjusts the black regions C1 to C4. When each of all of the signal levels is equal to or less than the preset threshold, the adjustment of the black regions C1 to C4 is finished. As a result, the black regions C1 to C4 where optical rays do not reach are assured in the effective pixel region D (concretely, in the four corners) in the solid-state imaging device 12c. Each of the pixel groups in the black regions C1 to C4 may be a pixel group of desired number of pixels (for example, a pixel group of four pixels by four pixels) but desirably a pixel group of larger number of pixels.

As described above, in the first embodiment of the present invention, the imaging unit photoelectrically converts light information received via the effective pixel region contributed to the image capture, thereby obtaining an image. The imaging unit detects the signal levels of the black regions in the effective pixel region. Based on the signal levels of the black regions detected by the imaging unit, the image determining unit calculates the number of 0-level pixels in the black region which changes due to fluctuations in the output of the power source of the imaging unit. Using the calculated number of 0-level pixels in the black region, the image determining unit performs the image determining process on each of the images. Output of an image determined as an image influenced by the fluctuations in the power source voltage is inhibited. The images other than the image inhibited to be output by the image determining unit in the series of images captured by the imaging unit, that is, stable images which are not influenced by fluctuations in the power source voltage are permitted to be output. Therefore, output (display) of an image influenced by fluctuations in the power source voltage of the imaging unit, concretely, an image influenced by fluctuations in the black reference level in enormous number of images captured by the imaging unit can be easily stopped. As a result, without displaying an image influenced by the power source voltage of the imaging unit, stable images can be provided (displayed) to the user.

In the above configuration, the image extracting unit extracts a successive image group including an image to be subjected to the image determining process. The image determining unit calculates an average value of the 0-level pixel numbers based on the signal levels of the black regions in images included in the extracted successive image group extracted, compares the calculated average value of the 0-level pixel numbers with the preset threshold, and performs the image determining process on each of the images. In the case where the average value of the 0-level pixel numbers exceeds the preset threshold, the image determining unit determines that the image is influenced by fluctuations in the power source voltage. Consequently, the image determining process can be performed without being influenced by peculiar pixels in the black region whose signal level accidentally drops due to noise or the like. As a result, the image determining process on the images can be performed with high precision.

Further, the image determining processes in two stages are performed on each of a series of images captured by the imaging unit. Therefore, an image influenced by fluctuations in output of the power source of the imaging unit can be reliably prevented from being output. In addition, inhibition of output of an image slightly influenced by fluctuations in the power source voltage, in images determined as images influenced by fluctuations in the power source voltage can be cancelled. As a result, without displaying images influenced by fluctuations in the power source voltage, larger number of stable in-vivo images can be provided to the user.

Since the black regions are set at four corners of the effective pixel region in the imaging unit, without disturbing output of an image, the wider black regions as compared with the case of setting the black regions in places other than the four corners can be set in the effective pixel region. Thus, precision of the pixel information in the black regions used for the image determining process can be improved.

Second Embodiment

Next, a second embodiment of the invention will be described. In the foregoing first embodiment, the influence of fluctuations in the power source voltage on each of in-vivo images is determined by using the 0-level pixel numbers in the black regions C1 to C4. In the second embodiment, the influence of fluctuations in the power source voltage on each of in-vivo images is determined by using a variation value of a signal level of a black region in the beginning of the operation of the imaging unit.

Figure 10:
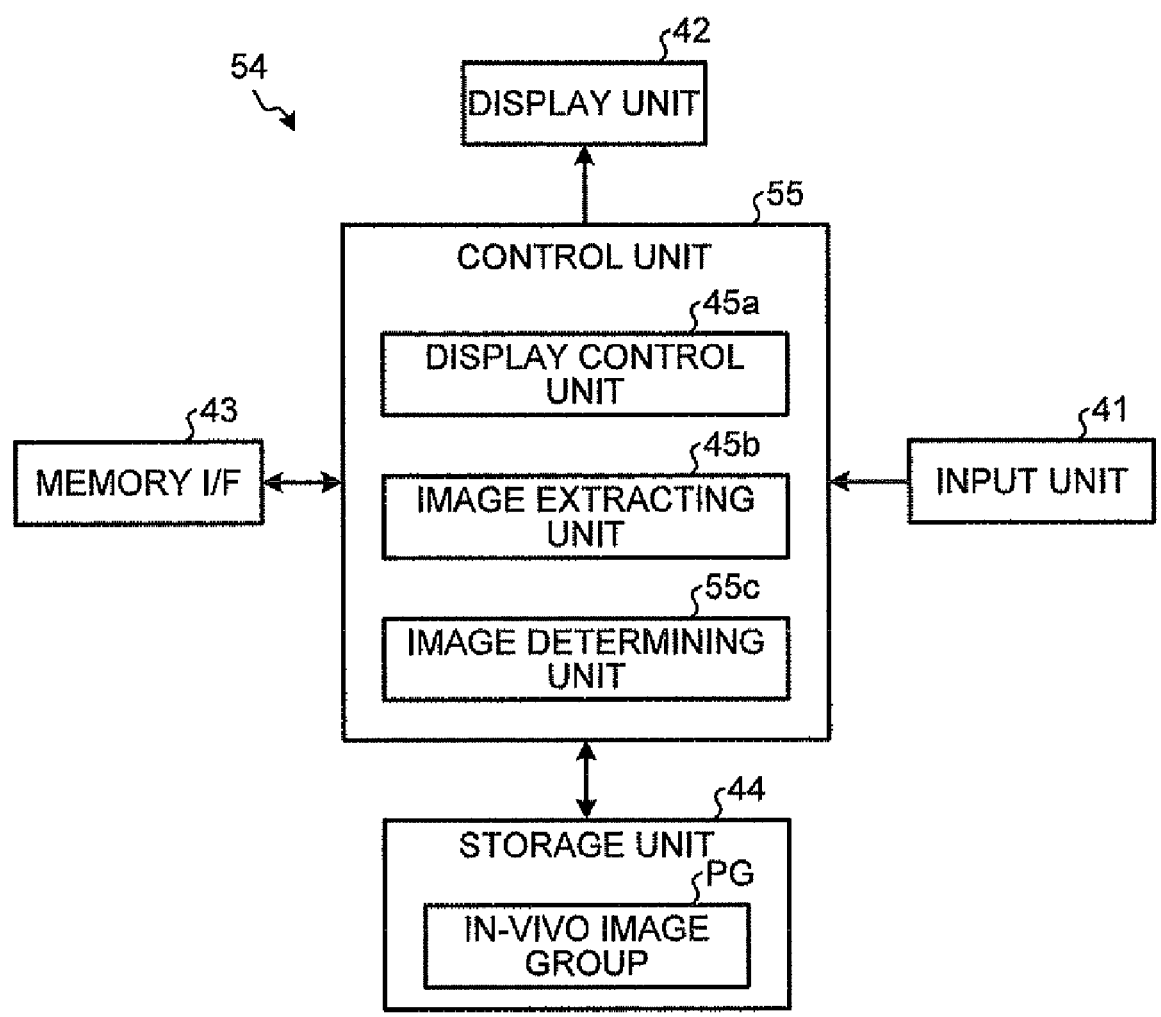
FIG. 10 is a block diagram schematically showing a configuration example of an image display apparatus as a second embodiment of the present invention.

FIG. 10 is a block diagram schematically showing a configuration example of an image display apparatus in the second embodiment of the present invention. As shown in FIG. 10, an image display apparatus 54 in the second embodiment has a control unit 55 in place of the control unit 45 of the image display apparatus 4 of the first embodiment. The other configuration is similar to that of the first embodiment, and the same reference numerals are designated to the same components. An image display system of the second embodiment has the image display apparatus 54 in place of the image display apparatus 4 of the image display system (refer to FIG. 1) of the first embodiment.

The control unit 55 has an image determining unit 55c in place of the image determining unit 45c of the image display apparatus 4 of the first embodiment. The control unit 55 has the function similar to that of the control unit 45 in the first embodiment except for the function of the image determining unit 55c.

The image determining unit 55c calculates a variation value of each of average brightnesses of the black regions C1 to C4 based on the signal levels of the black regions C1 to C4 in in-vivo images in a successive image group extracted by the image extracting unit 45b from the in-vivo image group PG, performs the image determining process on the in-vivo images based on the variation values of the average brightnesses calculated, and inhibits output of an in-vivo image determined as an image influenced by fluctuations in the power source voltage by the image determining process.

The variation values of the average brightnesses in the black regions C1 to C4 are variation values for average brightnesses in the black regions C1 to C4 when the imaging unit 12 starts operating in the capsule endoscope 2 shown in FIG. 2, that is, variation values for average brightnesses in the beginning of operation. The variation value is an example of pixel information of a black region which changes as an output of the power supply unit 15 for supplying power to the imaging unit 12 fluctuates. The variation values of the average brightnesses of the black regions C1 to C4 are equal to or less than the preset threshold in a state where a fluctuation in the output of the power supply unit 15 is small in the beginning of the operation or the like of the capsule endoscope 2. The variation value increases as the fluctuations in the output of the power supply unit 15 increase, that is, as the power of the power supply unit 15 is consumed. The image determining unit 55c sequentially performs the image determining process on the in-vivo images Pn (n=1, 2, 3, . . . ) by comparing the pixel information (for example, a variation value of each of the average brightnesses) in the black regions C1 to C4 with a predetermined threshold which is preliminarily set. The image determining unit 55c inhibits output of an in-vivo image which is determined as an image influenced by fluctuations in the power source voltage by the image determining process, and permits output of an in-vivo image which is determined as a stable image.

The image determining process using variation values of average brightnesses in the black regions C1 to C4 is the image determining process in the first stage performed by the image determining unit 55c. The image determining process is performed to determine the influence of fluctuations in the output (voltage fluctuations) of the power supply unit 15 in the capsule endoscope 2, for example, the influence on an in-vivo image of fluctuations in the black reference level. The image determining unit 55c performs the image determining process in the first stage and, then, in a manner similar to the image determining unit 45c in the first embodiment, performs the image determining process in the second stage.

In the case where a plurality of in-vivo image groups captured by a plurality of capsule endoscopes 2 of different ID information are stored in the storage unit 44, the image determining unit 55c performs the image determining process on the in-vivo images by the ID information of the capsule endoscopes 2.

Figure 11:
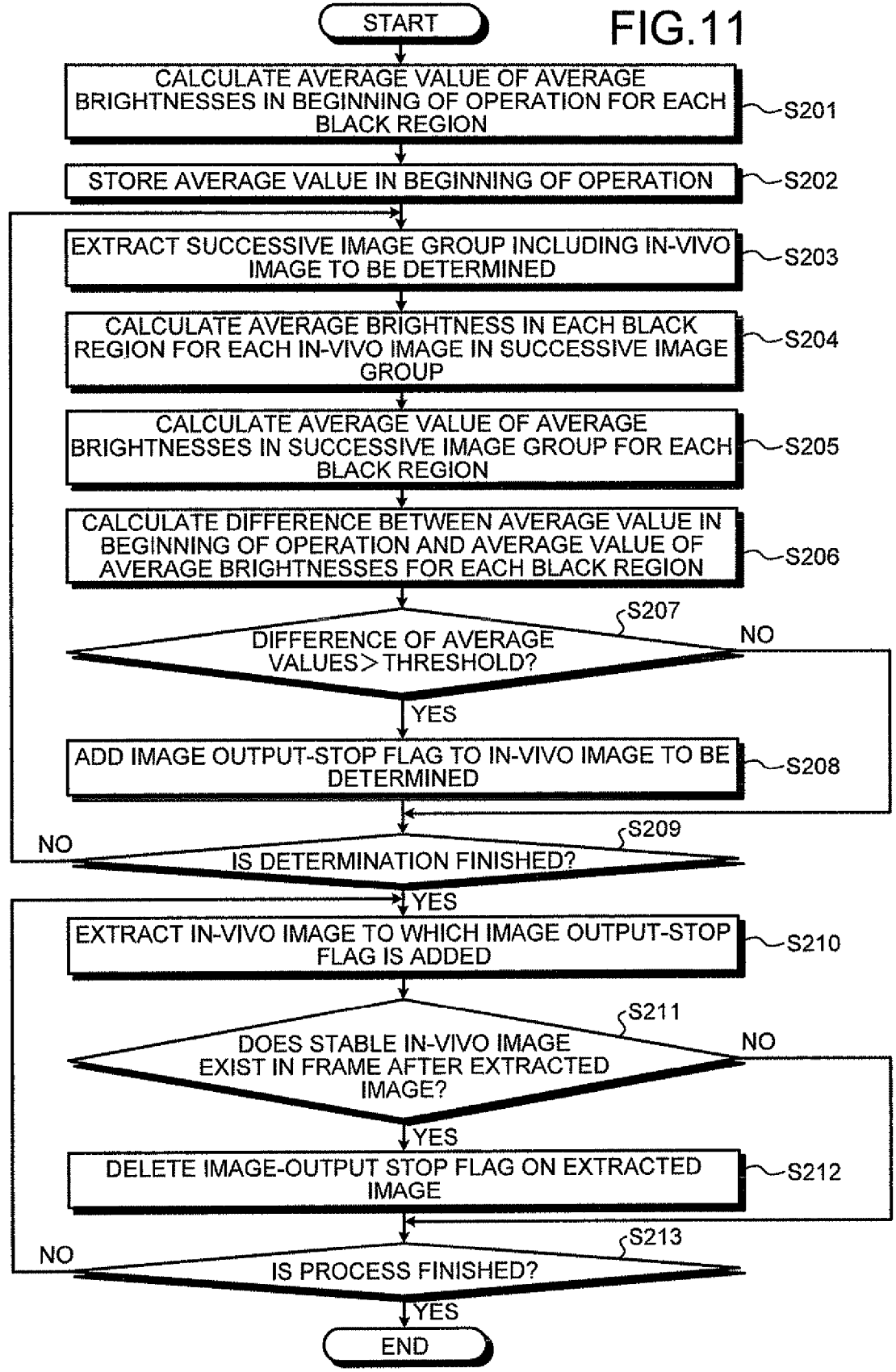
FIG. 11 is a flowchart illustrating a procedure of a control unit in the image display apparatus for performing an image determining process on an in-vivo image by using a variation value of average brightness in a black region in the beginning of operation.

Next, the operation of the image display apparatus 54 in the second embodiment of the invention will be described. FIG. 11 is a flowchart illustrating a procedure of a control unit in an image display apparatus for performing the image determining process on an in-vivo image by using a variation value of average brightness of a black region in the beginning of the operation. In the case where the in-vivo image group PG of the subject 1 is taken from the portable recording medium 5 inserted in the memory I/F 43, the control unit 55 in the image display apparatus 54 performs the image determining process on each of the in-vivo images Pn (n=1, 2, 3, . . . ) in the in-vivo image group PG with respect to the influence on an image (concretely, the influence on an image, of fluctuations of the black reference level) caused by consumption of the power of the power supply unit 15 of the capsule endoscope 2. According to a result of the image determining process, the control unit 55 inhibits or permits output of the in-vivo image Pn.

Specifically, as shown in FIG. 11, the control unit 55 calculates an average value of average brightnesses in the beginning of the operation of the capsule endoscope 2 by the black regions (step S201). In the step S201, the image extracting unit 45b extracts a successive image group of predetermined number of frames (for example, three frames) including an in-vivo image $P_1$ in the first frame from the in-vivo image group PG of the subject 1 taken from the portable recording medium 5 inserted in the memory I/F 43. The image determining unit 55c obtains the brightness level by the black regions in the in-vivo images included in the extracted successive image group and, based on the brightness levels obtained, calculates the average brightnesses in the black regions C1 to C4 of the in-vivo images. The image determining unit 55c calculates an average value of average brightnesses in each of the black regions C1 to C4 by dividing a value obtained by totaling the average brightnesses in each of the black regions by the number of frames in the successive image group. The average value is an average value of average brightnesses in each of the black regions C1 to C4 in the beginning of the operation of the capsule endoscope 2 (hereinbelow, also simply called an average value in the beginning of the operation).

Next, the control unit 55 stores the average value in the beginning of the operation calculated on the black region unit basis in step S201 into a RAM of itself or the like (step S202). In this case, the image determining unit 55c sets the average value in the beginning of the operation as a computation parameter used for the image determining process in the first stage.

Subsequently, the control unit 55 extracts a successive image group including an in-vivo image Pn to be determined from the in-vivo image group PG (step S203). In this case, the image determining unit 55c determines an in-vivo image Pn to be determined from the in-vivo image group PG in ascending order of frame numbers "n". The image extracting unit 45b extracts a successive image group of predetermined number of frames (for example, three frames) including the in-vivo image Pn to be determined by the image determining unit 55c.

Next, the control unit 55 calculates average brightnesses in the black regions C1 to C4 in each of the in-vivo images in the successive image group extracted in step S203 (step S204). In this case, the image determining unit 55c obtains the brightness level of each of the pixels of the black regions C1 to C4 for each of the in-vivo images included in the successive image group, and totals the brightness levels of the pixels obtained by the black regions in the in-vivo image. The image determining unit 55c divides the calculated total value of the brightness levels by the number of pixels in the black regions C1 to C4, thereby calculating the average brightness of each of the black regions C1 to C4. The image determining unit 55c repeatedly performs the computing process on each of the in-vivo images, thereby calculating the average brightnesses in the black regions C1 to C4 for each of the in-vivo images in the successive image group.

Next, based on the average brightnesses of the black regions C1 to C4 calculated on the in-vivo image unit basis in step S204, the control unit 55 calculates an average value of average brightnesses in the successive image group for each of the black regions (step S205). In this case, the image determining unit 55c divides the total value of the average brightnesses in the black region C1 in each of the in-vivo images in the successive image group by the number of frames of the successive image group, thereby calculating the average value of the average brightnesses in the black region C1 in the successive image group. Similarly, the image determining unit 55c divides the total value of the average brightnesses in the black region C2 in the successive image group by the number of frames of the successive image group, thereby calculating the average value of the average brightnesses in the black region C2 in the successive image group. The image determining unit 55c divides the total value of the average brightnesses in the black region C3 in the successive image group by the number of frames of the successive image group, thereby calculating the average value of the average brightnesses in the black region C3 in the successive image group. The image determining unit 55c divides the total value of the average brightnesses in the black region C4 in the successive image group by the number of frames of the successive image group, thereby calculating the average value of the average brightnesses in the black region C4 in the successive image group.

After that, the control unit 55 calculates the difference between the average value in the beginning of the operation calculated in the step S201 and the average value of average brightness in each of the black regions calculated in the step S205 (step S206). In this case, the image determining unit 55c calculates the difference between the average value in the beginning of the operation and the average value of average brightness in the black region C1 in the successive image group, calculates the difference between the average value in the beginning of the operation and the average value of average brightness in the black region C2 in the successive image group, calculates the difference between the average value in the beginning of the operation and the average value of average brightness in the black region C3 in the successive image group, and calculates the difference between the average value in the beginning of the operation and the average value of average brightness in the black region C4 in the successive image group. The difference between the average value in the beginning of the operation and the average value of average brightness in each of the black regions C1 to C4 corresponds to a variation value (transition) of the average brightnesses in the black regions C1 to C4 in the beginning of the operation of the capsule endoscope 2.

Next, the control unit 55 determines whether the difference of the average values calculated in step S206 exceeds a predetermined threshold or not (step S207). In the case where the difference exceeds the predetermined threshold (Yes in step S207), it is determined that the in-vivo image Pn to be determined is influenced by fluctuations in the power source voltage, and an image output stop flag is added to the in-vivo image Pn to be determined (step S208). In steps S207 and S208, the image determining unit 55c compares the difference between the average value in the beginning of the operation and the average value of the average brightnesses in the black regions C1 to C4, that is, a variation value of the average brightnesses in the black regions C1 to C4 in the beginning of the operation with a preset threshold. In the case where any of the differences of the average values of the average brightnesses exceeds the threshold as a result of the comparing process, the image determining unit 55c determines that the in-vivo image Pn to be determined in the step S203 is influenced by fluctuations in the power source voltage, and adds the image output stop flag to the in-vivo image.

After that, in a manner similar to the step S106, the control unit 55 determines whether or not the determination on all of in-vivo images included in the in-vivo image group PG of the subject 1 has been finished (step S209). If the determination has not been finished (No in step S209), the control unit 55 returns to step S203 and repeats the processes of the step S203 and the subsequent steps.

In the case where the difference between the average value in the beginning of the operation and the average value of the average brightnesses of the black regions C1 to C4 is equal to or less than the predetermined threshold in the step S207 (No in step S207), the control unit 55 determines that the in-vivo image Pn to be determined is a stable image and, without adding the image output stop flag to the in-vivo image Pn to be determined, advances to step S209. In this case, the image determining unit 55c compares the difference between the average value in the beginning of the operation and the average value of the average brightnesses in the black region C1 with the threshold. The image determining unit 55c compares the difference between the average value in the beginning of the operation and the average value of the average brightnesses in the black region C2 with the threshold. The image determining unit 55c compares the difference between the average value in the beginning of the operation and the average value of the average brightnesses in the black region C3 with the threshold. The image determining unit 55c compares the difference between the average value in the beginning of the operation and the average value of the average brightnesses in the black region C4 with the threshold. In the case where the difference of the average values, that is, the vibration value of each of the average brightnesses in the black regions C1 to C4 in the beginning of the operation is equal to or less than the threshold value, the image determining unit 55c determines the in-vivo image Pn to be determined as a stable image, and does not add the image output stop flag to the in-vivo image.

On the other hand, in the case where it is determined that determination of all of in-vivo images in the in-vivo image group PG in the step S209 is finished (Yes in step S209), the control unit 55 repeats the processes similar to those in the steps S107 to S110 as necessary and performs the image determining process in the second stage in a manner similar to the first embodiment (steps S210 to S213). In the steps S210 to S213, like the image determining unit 45c in the first embodiment, the image determining unit 55c performs the image determining process in the second stage on one or more in-vivo images determined as an image influenced by fluctuations in the power source voltage by the image determining process in the first stage. As a result, like the image determining unit 45c in the first embodiment, the image determining unit 55c deletes the image output stop flags on all of in-vivo images existing in frames before the in-vivo image to which the image output stop flag is not added without deleting the image output stop flags on all of in-vivo images determined as images influenced by fluctuations in the power source voltage and existing in the last frame in the in-vivo image to which the image output stop flag is not added and included in the in-vivo image group PG and the subsequent frames.

Figure 12:
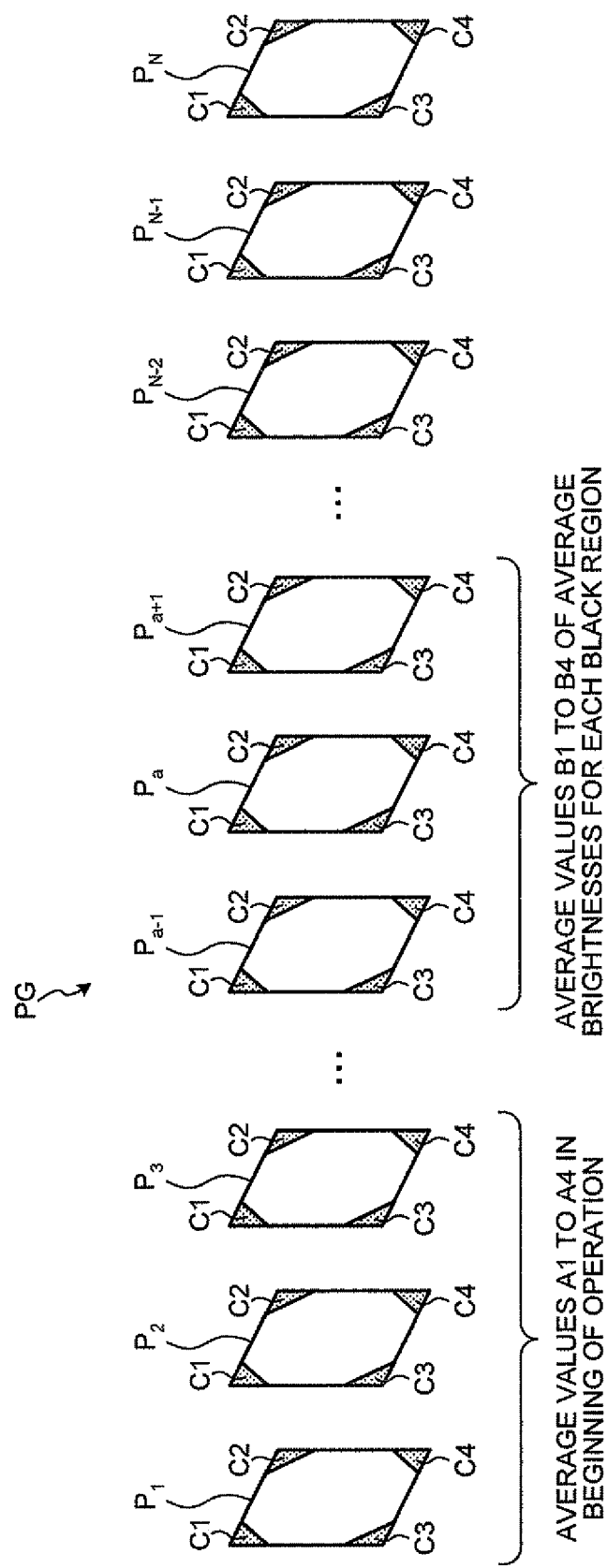
FIG. 12 is a schematic view for explaining an image determining process in the first stage by an image determining unit in the image display apparatus as the second embodiment.

Next, the case of extracting a group of three successive images (three frames) including an in-vivo image to be determined from the in-vivo image group PG made of N in-vivo images Pn (n=1, 2, 3, . . . , N) and performing the image determining process will be described as an example. The image determining process in the first stage performed by the image determining unit 55c will be concretely described. FIG. 12 is a schematic view for explaining the image determining process in the first stage performed by the image determining unit in the image display apparatus of the second embodiment.

In FIG. 12, an in-vivo image $P_a$ (1<a<N) in the a-th frame is an object of determination of the image determining unit 55c. A successive image group of the in-vivo image $P_a$ to be determined and immediately preceding and subsequent frame of in-vivo images $P_{a-1}$ and $P_{a+1}$ is an image group extracted from the in-vivo image group PG by the image extracting unit 45b at the time of performing the image determining process in the first stage on the in-vivo image $P_a$.

First, the image determining unit 55c sequentially calculates, in the successive image group of predetermined number of frames (in FIG. 12, 3 frames) including the in-vivo image $P_1$ in the first frame, an average brightness of each of the black regions C1 to C4 in the in-vivo image $P_1$, an average brightness in each of the black regions C1 to C4 in the in-vivo image $P_2$, and an average brightness of each of the black regions C1 to C4 in the in-vivo image $P_3$. Subsequently, the image determining unit 55c averages the average brightness in each of the black regions, and sequentially calculates the average values of the average brightnesses in the black regions C1 to C4 in the in-vivo images $P_1$, $P_2$, and $P_3$. Specifically, the image determining unit 55c calculates an average value A1 of the average brightness in the black region C1 in the beginning of the operation of the capsule endoscope 2. The image determining unit 55c calculates an average value A2 of the average brightness in the black region C2 in the beginning of the operation. The image determining unit 55c calculates an average value A3 of the average brightness in the black region C3 in the beginning of the operation. The image determining unit 55c calculates an average value A4 of the average brightness in the black region C4 in the beginning of the operation.

Next, the image determining unit 55c calculates an average value of the average brightnesses in the black regions C1 to C4 in in-vivo images $P_{a-1}$, $P_a$, and $P_{a+1}$ including an object to be determined and, using the calculated average value, performs the image determining process in the first stage on the in-vivo image $P_a$ to be determined. Concretely, the image determining unit 55c calculates the average brightnesses in each of the black regions C1 to C4 in the in-vivo image $P_{a-1}$, calculates the average brightnesses in each of the black regions C1 to C4 in the in-vivo image $P_a$, and calculates the average brightnesses in the black regions C1 to C4 in the in-vivo image $P_{a+1}$. The image determining unit 55c calculates an average value B1 of the average brightnesses in the black regions C1 in the in-vivo images $P_{a-1}$, $P_a$, and $P_{a+1}$ by dividing the total value of the average brightnesses in the black regions C1 in the in-vivo images $P_{a-1}$, $P_a$ And $P_{a+1}$ by the number of frames "3" in the successive image group.

Similarly, the image determining unit 55c calculates an average value B2 of the average brightnesses in the black regions C2 in the in-vivo images $P_{a-1}$, $P_a$, and $P_{a+1}$ by dividing the total value of the average brightnesses in the black regions C2 in the in-vivo images $P_{a-1}$, $P_a$, and $P_{a+1}$ by the number of frames "3" in the successive image group. The image determining unit 55c calculates an average value B3 of the average brightnesses in the black regions C3 in the in-vivo images $P_{a-1}$, $P_a$, and $P_{a+1}$ by dividing the total value of the average brightnesses in the black regions C3 in the in-vivo images $P_{a-1}$, $P_a$, and $P_{a+1}$ by the number of frames "3" in the successive image group. The image determining unit 55c calculates an average value B4 of the average brightnesses in the black regions C4 in the in-vivo images $P_{a-1}$, $P_a$, and $P_{a+1}$ by dividing the total value of the average brightnesses in the black regions C4 in the in-vivo images $P_{a-1}$, $P_a$, and $P_{a+1}$ by the number of frames "3" in the successive image group.

After that, the image determining unit 55c subtracts the average values B1 to B4 of the average brightnesses in the black regions C1 to C4 from the average values A1 to A4 in the beginning of operation which are calculated in advance, respectively, thereby sequentially calculating an average value difference (A1−B1) of the average brightnesses in the black region C1, an average value difference (A2−B2) of the average brightnesses in the black region C2, an average value difference (A3−B3) of the average brightnesses in the black region C3, and an average value difference (A4−B4) of the average brightnesses in the black region C4.

The average value differences (A1−B1), (A2−B2), (A3−B3), and (A4−B4) in the black regions C1 to C4 are variation values of the average brightnesses in the black regions C1 to C4 in the beginning of the operation of the capsule endoscope 2. The image determining unit 55c compares each of the average value differences (A1−B1), (A2−B2), (A3−B3), and (A4−B4) calculated in the respective black regions with a preset threshold. In the case where at least one of the average value differences (A1−B1), (A2−B2), (A3−B3), and (A4−B4) exceeds the threshold, the image determining unit 55c determines that the in-vivo image $P_a$ to be determined is influenced by fluctuations in the power source voltage. In the case where all of the average value differences (A1−B1), (A2−B2), (A3−B3), and (A4−B4) are equal to or less than the threshold, the image determining unit 55c determines that the in-vivo image $P_a$ to be determined as a stable image. In the case where the in-vivo image $P_a$ to be determined is determined as an image influenced by fluctuations in the power source voltage, the image determining unit 55c adds the image output stop flag F to the in-vivo image Pa.

In a manner similar to the case of the in-vivo image $P_a$, the image determining unit 55c repeatedly performs the image determining process in the first stage on each of the in-vivo images Pn (n=1, 2, 3, ..., N) in the in-vivo image group PG. To all of in-vivo images determined as images influenced by fluctuations in the power source voltage by the image determining process in the first stage, the image output stop flag F is added.

In the case where the image determining unit 55c performs the image determining process on the in-vivo image $P_1$ in the first frame, the image extracting unit 45b may extract a successive image group of the in-vivo image $P_1$ to be determined and two frames of in-vivo images $P_2$ and $P_3$ subsequent to the in-vivo image $P_1$. In the case where the image determining unit 55c performs the image determining process on the in-vivo image $P_N$ in the N-th frame, the image extracting unit 45b may extract a successive image group of the in-vivo image $P_N$ to be determined and two frames of in-vivo images $P_{N-2}$ and $P_{N-1}$ before the in-vivo image $P_N$.

As described above, in the second embodiment of the present invention, the image determining unit calculates variation values of the average brightness levels in the black regions in the beginning of the operation of the imaging unit based on the signal levels of the black regions detected by the imaging unit and, using the calculated variation values of the average brightness levels in the black regions, performs the image determining process on each of the images. The other configuration is similar to that of the first embodiment. Consequently, in a manner similar to the first embodiment, output (display) of an image influenced by fluctuations in the black reference level can be easily stopped. As a result, the image pickup apparatus, the image display apparatus, and the image display system enjoying the effects similar to those of the first embodiment can be realized.

Third Embodiment

Next, a third embodiment of the invention will be described. In the foregoing first embodiment, the influence of fluctuations in the power source voltage on each of in-vivo images is determined by using the 0-level pixel numbers in the black regions C1 to C4. In the third embodiment, the influence of fluctuations in the power source voltage on each of in-vivo images is determined by using a signal level difference among a plurality of black regions in an in-vivo image to be determined.

Figure 13:
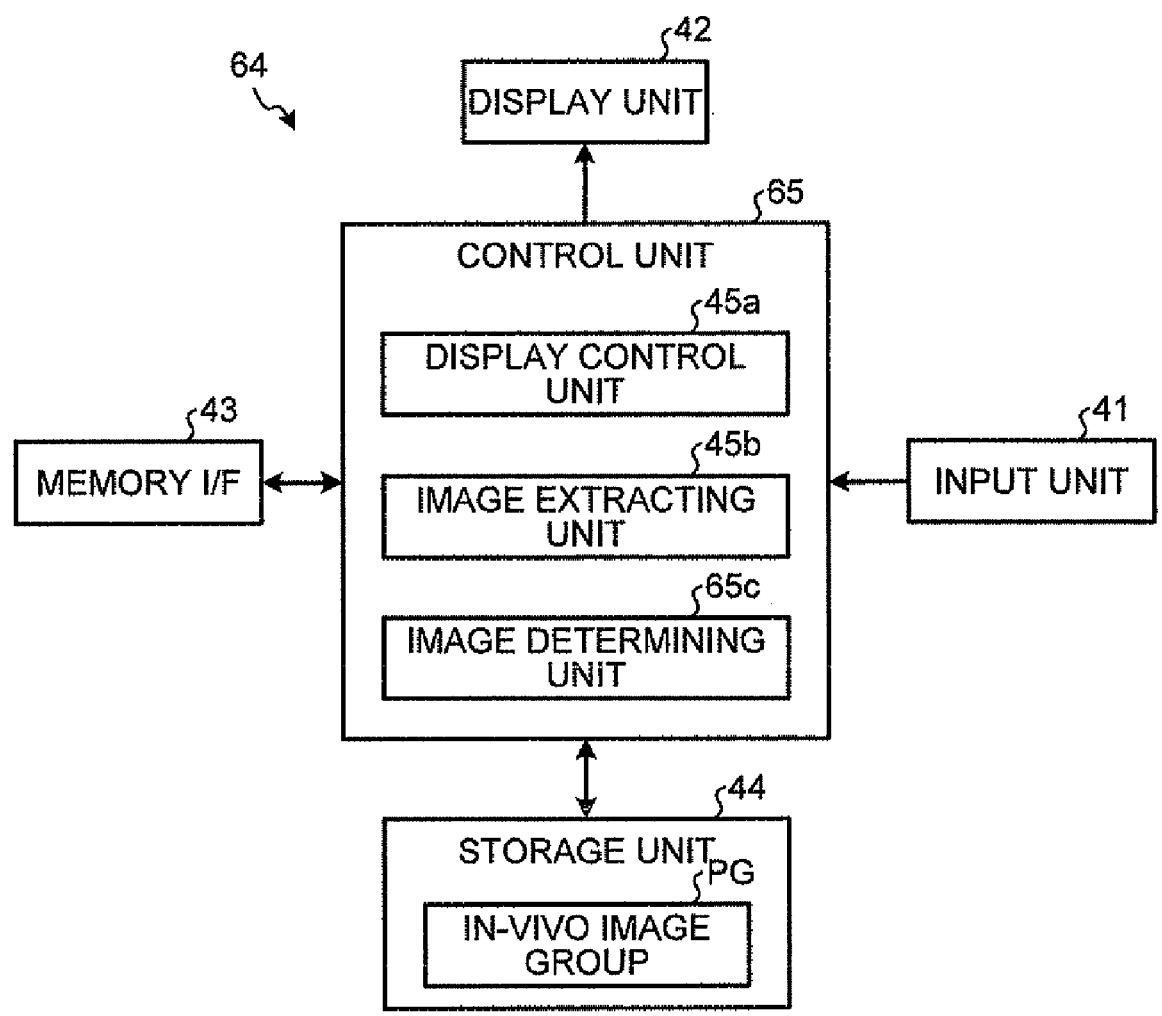
FIG. 13 is a block diagram schematically showing a configuration example of an image display apparatus as a third embodiment of the invention.

FIG. 13 is a block diagram schematically showing a configuration example of an image display apparatus in the third embodiment of the present invention. As shown in FIG. 13, an image display apparatus 64 of the third embodiment has a control unit 65 in place of the control unit 45 of the image display apparatus 4 of the first embodiment. The other configuration is similar to that of the first embodiment, and the same reference numerals are designated to the same components. An image display system of the third embodiment has the image display apparatus 64 in place of the image display apparatus 4 of the image display system (refer to FIG. 1) of the first embodiment.

The control unit 65 has an image determining unit 65c in place of the image determining unit 45c of the image display apparatus 4 of the first embodiment. The control unit 65 has the function similar to that of the control unit 45 in the first embodiment except for the function of the image determining unit 65c.

The image determining unit 65c calculates a brightness level difference among the black regions C1 to C4 in each of in-vivo images based on the signal levels of the black regions C1 to C4 in the in-vivo images in a successive image group extracted by the image extracting unit 45b from the in-vivo image group PG, performs the image determining process on the in-vivo images using the calculated brightness level difference among the black regions C1 to C4, and inhibits output of an in-vivo image determined as an image influenced by fluctuations in the power source voltage by the image determining process.

The brightness level difference among the black regions C1 to C4 is a brightness level difference between a pair of black regions in the same in-vivo image and is an example of pixel information of a black region which changes as an output of the power supply unit 15 for supplying power to the imaging unit 12 fluctuates. The brightness level difference among the black regions C1 to C4 is equal to or less than the preset threshold in a state where a fluctuation in the output of the power supply unit 15 is small in the beginning of the operation or the like of the capsule endoscope 2. The brightness level difference increases as the fluctuations in the output of the power supply unit 15 increase, that is, as the power of the power supply unit 15 is consumed. The image determining unit 65c sequentially performs the image determining process on the in-vivo images Pn (n=1, 2, 3, . . . ) by comparing the pixel information (for example, a brightness level difference between a pair of black regions in the same in-vivo image) in the black regions C1 to C4 with a predetermined threshold which is preliminarily set. The image determining unit 65c inhibits output of an in-vivo image which is determined as an image influenced by fluctuations in the power source voltage by the image determining process, and permits output of an in-vivo image which is determined as a stable image which is not influenced by fluctuations in the power source voltage.

The image determining process using the brightness level difference among the black regions C1 to C4 is performed to determine the influence of fluctuations in the output (voltage fluctuations) of the power supply unit 15 in the capsule endoscope 2, for example, the influence on an image of fluctuations in the black reference level. Different from the image determining unit 45c in the first embodiment, the image determining unit 65c performs the image determining process in the first stage using the brightness level difference among the black regions C1 to CA and, then, determines the influence on each of in-vivo images.

In the case where a plurality of in-vivo image groups captured by a plurality of capsule endoscopes 2 of different ID information are stored in the storage unit 44, the image determining unit 65c performs the image determining process on the in-vivo images by the ID information of the capsule endoscopes 2.

Figure 14:
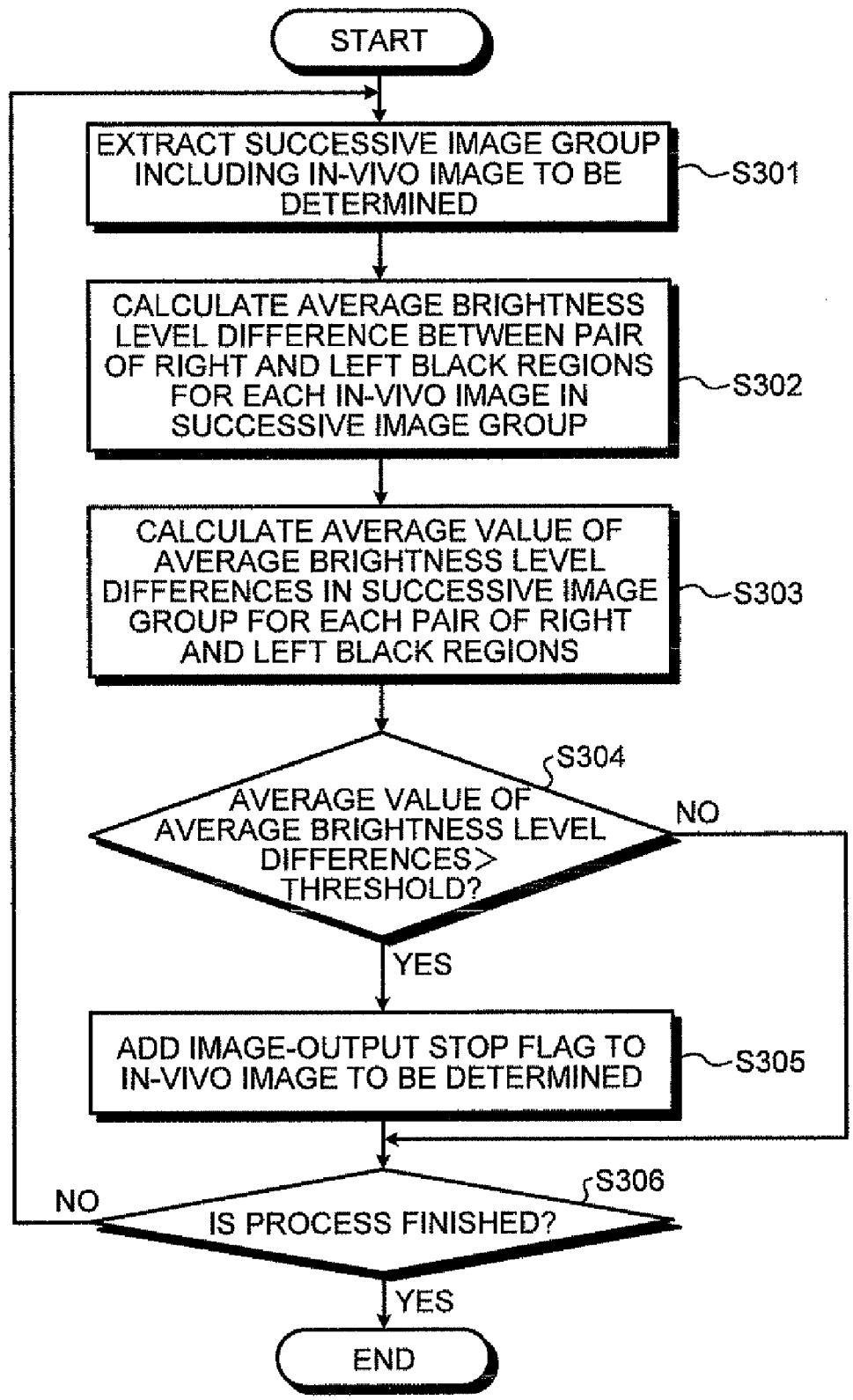
FIG. 14 is a flowchart illustrating a procedure of a control unit in the image display apparatus for performing an image determining process on an in-vivo image using a brightness level difference between a pair of black regions in a single in-vivo image.

Next, the operation of the image display apparatus 64 in the third embodiment of the invention will be described. FIG. 14 is a flowchart illustrating a procedure of a control unit in an image display apparatus for performing the image determining process on an in-vivo image by using a brightness level difference between a pair of black regions in the same in-vivo image. In the case where the in-vivo image group PG of the subject 1 is taken from the portable recording medium 5 inserted in the memory I/F 43, the control unit 65 in the image display apparatus 64 performs the image determining process on each of the in-vivo images Pn (n=1, 2, 3, . . . ) in the in-vivo image group PG with respect to the influence on an image caused by consumption of the power of the power supply unit 15 of the capsule endoscope 2 (concretely, the influence on an image, of fluctuations of the black reference level). According to a result of the image determining process, the control unit 65 inhibits or permits output of the in-vivo image Pn.

Specifically, as shown in FIG. 14, the control unit 65 extracts a successive image group including an in-vivo image Pn to be determined from the in-vivo image group PG of the subject 1 taken from the portable recording medium 5 inserted in the memory I/F 43 (step S301). In this case, the image determining unit 65c determines the in-vivo image Pn to be determined from the in-vivo image group PG in ascending order of the frame numbers "n". The image extracting unit 45b extracts a successive image group of predetermined number of frames (for example, three frames) including the in-vivo image Pn to be determined by the image determining unit 65c.

Next, the control unit 65 calculates the average brightness level difference between a pair of right and left black regions for each of in-vivo images in the successive image group extracted in step S301 (step S302). In this case, the image determining unit 65c obtains the brightness level of each of pixels in the black regions C1 to C4 for each of the in-vivo images included in the successive image group, and totals the obtained brightness levels of the pixels for each of the black regions in the in-vivo image. The image determining unit 65c divides the calculated total value of the brightness levels by each of the numbers of pixels in the black regions C1 to C4, thereby calculating the average brightness in each of the black regions C1 to C4. After that, the image determining unit 65c sequentially calculates the average brightness difference, that is, the average brightness level difference between a pair of right and left black regions C1 and C2 on the upper side out of the black regions C1 to C4 in the same in-vivo image, and the average brightness level difference between the remaining pair of right and left black regions C3 and C4 on the lower side. By repeating the computing process for each of the in-vivo images, the image determining unit 65c calculates the average brightness level difference between the pair of right and left black regions C1 and C2 on the upper side and the average brightness level difference between the pair of right and left black regions C3 and C4 on the lower side for each of the in-vivo images in the successive image group.

Subsequently, the control unit 65 calculates an average value of average brightness level differences in the successive image groups for each of the pairs of right and left black regions based on the average brightness level difference of the right and left pair of black regions C1 and C2 on the upper side and the average brightness level difference of the right and left pair of black regions C3 and C4 on the lower side in the in-vivo images calculated in step S302 (step S303). In this case, the image determining unit 65c divides the total value of the average brightness level differences of the pairs of right and left black regions C1 and C2 on the upper side in the in-vivo images in the successive image group by the number of frames of the successive image group, thereby calculating an average value of average brightness level differences of the pair of right and left black regions C1 and C2 on the upper side in the successive image group. Similarly, the image determining unit 65c divides the total value of the average brightness level differences of the pairs of right and left black regions C3 and C4 on the lower side in the successive image group by the number of frames of the successive image group, thereby calculating an average value of average brightness level differences of the pair of right and left black regions C3 and C4 on the lower side in the successive image group.

Next, the control unit 65 determines whether the average value of the average brightness level differences calculated in step S303 exceeds a predetermined threshold or not (step S304). In the case where the average value exceeds the threshold (Yes in step S304), the control unit 65 determines that the in-vivo image Pn to be determined is influenced by fluctuations in the power source voltage, and adds the image output stop flag to the in-vivo image Pn to be determined (step S305). In the steps S304 and S305, the image determining unit 65c compares the average value of the average brightness level differences of the pair of right and left black regions C1 and C2 on the upper side in the successive image group with the preset threshold and, further, compares the average value of the average brightness level differences of the pair of right and left black regions C3 and C4 on the lower side in the successive image group with the preset threshold. When any of the average values of the average brightness level differences exceeds the threshold as a result of the comparing process, the image determining unit 65c determines that the in-vivo image Pn to be determined in the step S301 is influenced by fluctuations in the power source voltage, and adds the image output stop flag to the in-vivo image.

After that, in a manner similar to the step S106, the control unit 65 determines whether or not the determination on all of in-vivo images included in the in-vivo image group PG of the subject 1 has been finished (step S306). If the process has not been finished (No in step S306), the control unit 65 returns to the step S301 and repeats the processes of the step S301 and the subsequent steps.

On the other hand, in the case where each of the average value of the average brightness level differences of the pair of right and left black regions C1 and C2 on the upper side and the average value of the average brightness level differences of the pair of right and left black regions C3 and C4 on the lower side is equal to or less than the predetermined threshold in the step S304 (No in step S304), the control unit 65 determines that the in-vivo image Pn to be determined is a stable image which is not influenced by fluctuations in the power source voltage and, without adding the image output stop flag to the in-vivo image Pn to be determined, advances to step S306. In this case, the image determining unit 65c compares the average value of the average brightness level differences in the pair of right and left black regions C1 and C2 on the upper side with the threshold, and compares the average value of the average brightness level differences in the pair of right and left black regions C3 and C4 on the lower side with the threshold. In the case where each of the average values of the average brightness level differences is equal to or less than the threshold, the image determining unit 65c determines that the in-vivo image Pn to be determined is a stable image which is not influenced by fluctuations in the power source voltage. The image determining unit 65c does not add the image output stop flag to the stable in-vivo image.

In the case where the image determining process (the image determining process in the first stage) has been completed on all of in-vivo images in the in-vivo image group PG, the control unit 65 determines end of the process in the step S306 (Yes in step S306), and finishes the process.

Figure 15:
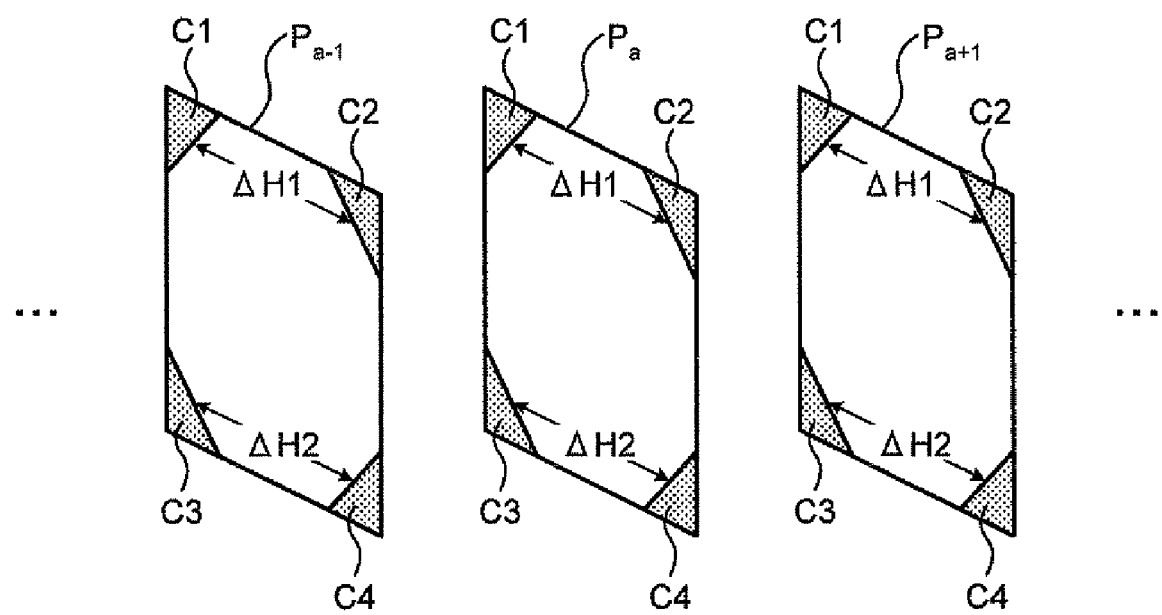
FIG. 15 is a schematic view for explaining an image determining process by an image determining unit in the image display apparatus of the third embodiment.

Next, the case of extracting a group of three successive images (three frames) including an in-vivo image to be determined from the in-vivo image group PG made of N in-vivo images Pn (n=1, 2, 3, . . . , N) and performing the image determining process will be described as an example. The image determining process performed by the image determining unit 65c will be concretely described. FIG. 15 is a schematic view for explaining the image determining process performed by the image determining unit in the image display apparatus of the third embodiment.

In FIG. 15, an in-vivo image $P_a$ (1<a<N) in the a-th frame is an object of determination of the image determining unit 65c. A successive image group of the in-vivo image $P_a$ to be determined and in-vivo images $P_{a-1}$ and $P_{a+1}$ in immediately preceding and subsequent frames is an image group extracted from the in-vivo image group PG by the image extracting unit 45b at the time of performing the image determining process on the in-vivo image $P_a$.

The image determining unit 65c calculates an average brightness level difference among the black regions C1 to C4 in the in-vivo images $P_{a-1}$, $P_a$, and $P_{a+1}$ including the in-vivo image to be determined, and performs the image determining process on the in-vivo image $P_a$ to be determined by using the calculated average brightness level difference. Concretely, the image determining unit 65c calculates the average brightnesses in the black regions C1 to C4 with respect to the in-vivo image $P_{a-1}$ and calculates an average brightness level difference ΔH1 of the pair of right and left black regions C1 and C2 on the upper side in the in-vivo image $P_{a-1}$, and an average brightness level difference ΔH2 of the pair of right and left black regions C3 and C4 on the lower side in the in-vivo image $P_{a-1}$. The image determining unit 65c also calculates the average brightnesses in the black regions C1 to C4 with respect to the in-vivo image $P_a$, and calculates an average brightness level difference ΔH1 of the pair of right and left black regions C1 and C2 on the upper side in the in-vivo image $P_a$, and an average brightness level difference ΔH2 of the pair of right and left black regions C3 and C4 on the lower side in the in-vivo image $P_a$. Further, the image determining unit 65c also calculates the average brightnesses in the black regions C1 to C4 with respect to the in-vivo image $P_{a+1}$ and calculates an average brightness level difference ΔH1 of the pair of right and left black regions C1 and C2 on the upper side in the in-vivo image $P_{a+1}$, and an average brightness level difference ΔH2 of the pair of right and left black regions C3 and C4 on the lower side in the in-vivo image $P_{a+1}$.

Next, the image determining unit 65c calculates an average value ΔJ1 of the average brightness level differences ΔH1 in the pair of right and left black regions C1 and C2 on the upper side in the in-vivo images $P_{a-1}$, $P_a$, and $P_{a+1}$ by dividing the total value of the average brightness level differences ΔH1 in the in-vivo images $P_{a-1}$, $P_a$, and $P_{a+1}$ by the number of frames "3" in the successive image group. Similarly, the image determining unit 65c calculates an average value ΔJ2 of the average brightness level differences ΔH2 in the pair of right and left black regions C3 and C4 on the lower side in the in-vivo images $P_{a-1}$, $P_a$, and $P_{a+1}$ by dividing the total value of the average brightness level differences ΔH2 in the in-vivo images $P_{a-1}$, $P_a$, and $P_{a+1}$ by the number of frames "3" in the successive image group.

The average brightness level differences ΔH1 in the black regions C1 and C2 and the average brightness level differences ΔH2 in the black regions C3 and C4 are numerical values indicative of fluctuations (deviations) of the black reference level in the same in-vivo image, and increase as the fluctuations in the output of the power supply unit 15 of the capsule endoscope 2 increases (that is, the power is consumed). That is, the average value ΔJ1 of the average brightness level differences ΔH1 in the successive image group and the average value ΔJ2 of the average brightness level differences ΔH2 increase as fluctuations in the output of the power supply unit 15 increases.

The image determining unit 65c compares the average value ΔJ1 of the average brightness level differences ΔH1 with the preset threshold, and compares the average value ΔJ2 of the average brightness level differences ΔH2 with the preset threshold. In the case where at least one of the average values ΔJ1 and ΔJ2 exceeds the preset threshold, the image determining unit 65c determines that the in-vivo image $P_a$ to be determined is influenced by fluctuations in the power source voltage. In the case where both of the average values ΔJ1 and ΔJ2 are equal to or less than the preset thresholds the image determining unit 65c determines that the in-vivo image $P_a$ to be determined is a stable image. In the case where the in-vivo image $P_a$ to be determined is determined as an image influenced by fluctuations in the power source voltage, the image determining unit 65c adds the image output stop flag F to the in-vivo image $P_a$. In a manner similar to the case of the in-vivo image $P_a$, the image determining unit 65c repeatedly performs the image determining process on each of the in-vivo images Pn (n=1, 2, 3, . . . , N) in the in-vivo image group PG. To all of in-vivo images determined as images influenced by fluctuations in the power source voltage by the image determining process in the first stage, the image output stop flag F is added.

In the case where the image determining unit 65c performs the image determining process on the in-vivo image $P_1$ in the first frame, the image extracting unit 45b may extract a successive image group of the in-vivo image $P_1$ to be determined and two frames of in-vivo images $P_2$ and $P_3$ subsequent to the in-vivo image $P_1$. In the case where the image determining unit 65c performs the image determining process on the in-vivo image $P_N$ in the N-th frame, the image extracting unit 45b may extract a successive image group of the in-vivo image $P_N$ to be determined and two frames of in-vivo images $P_{N-2}$ and $P_{N-1}$ before the in-vivo image $P_N$.

As described above, in the third embodiment of the present invention, the image determining unit calculates the average value of brightness level differences among the plurality of black regions in the same image based on the signal levels of the black regions detected by the imaging unit and, using the calculated average value of the brightness level differences, performs the image determining process on each of the images. The other configuration is similar to that of the first embodiment. Consequently, in a manner similar to the first embodiment, output (display) of an image influenced by fluctuations in the black reference level can be easily stopped. As a result, the image pickup apparatus, the image display apparatus, and the image display system enjoying the effects similar to those of the first embodiment can be realized.

Since the image determining process is performed on images by using the brightness level differences among the black regions in the same image, the influence on an image caused by bias of the black reference level occurring in an image with fluctuations in the power source voltage of the imaging unit (consumption of the power source) can be directly determined. As a result, it is unnecessary to perform the image determining process in two or more stages on each of the images. Output of an image influenced by fluctuations in the power source voltage can be stopped reliably by the image determining process in the first stage.

Fourth Embodiment

Next, a fourth embodiment of the invention will be described. In the foregoing first embodiment, the image determining process is performed on an in-vivo image by the image display apparatus for displaying an in-vivo image of the subject 1 captured by the capsule endoscope 2. In the fourth embodiment, the image determining process is performed by a capsule endoscope for capturing an in-vivo image.

Figure 16:
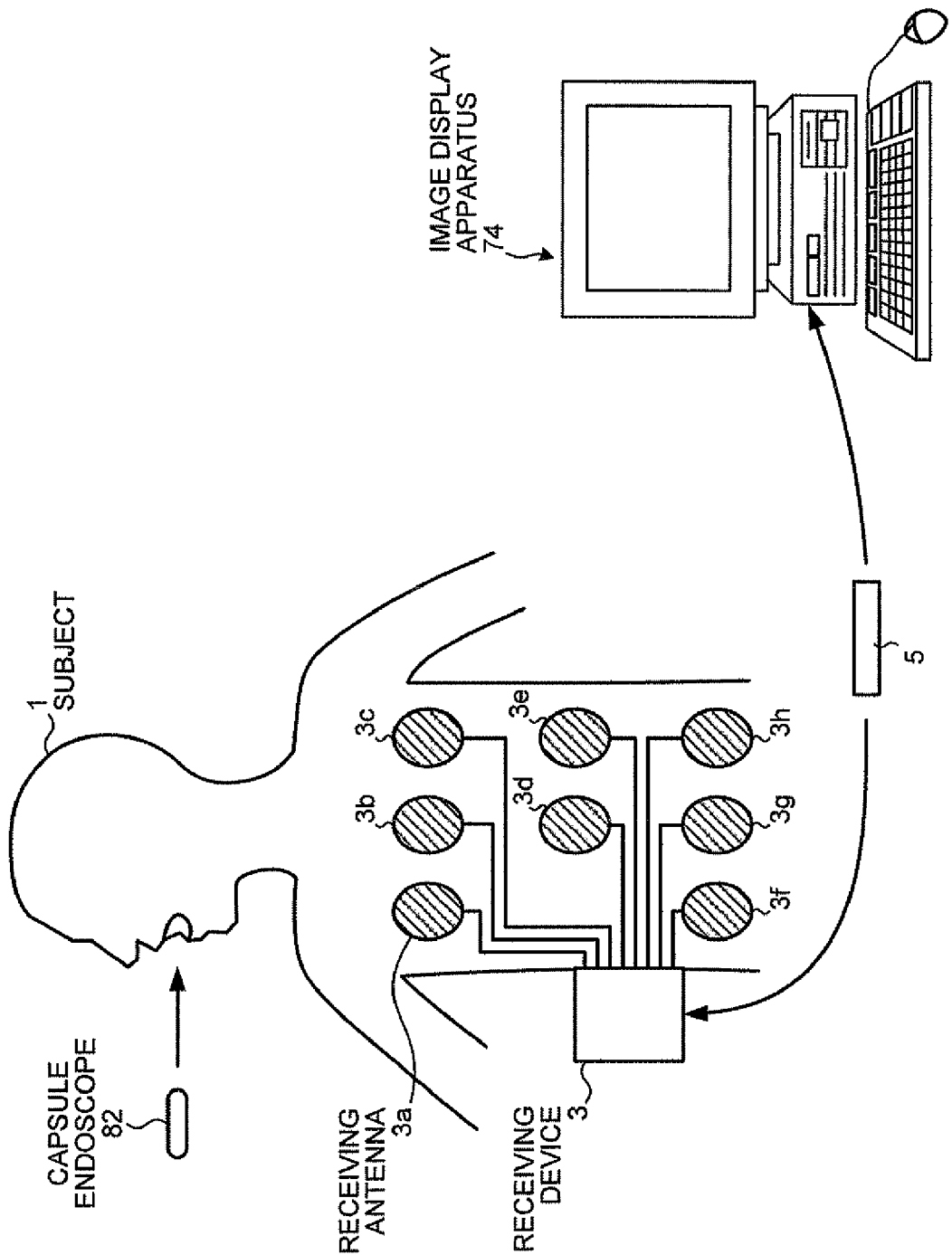
FIG. 16 is a schematic view illustrating a configuration example of an image display system as a fourth embodiment of the invention.

FIG. 16 is a schematic diagram illustrating a configuration example of an image display system in the fourth embodiment of the present invention. As shown in FIG. 16, the image display system of the fourth embodiment of the invention has a capsule endoscope 82 in place of the capsule endoscope 2 in the image display system (refer to FIG. 1) of the first embodiment and has an image display apparatus 74 in place of the image display apparatus 4. The other configuration is similar to that of the first embodiment, and the same reference numerals are designated to the same components.

The capsule endoscope 82 is an example of the image pickup apparatus of the present invention and has functions similar to those of the capsule endoscope 2 of the first embodiment except that the capsule endoscope 82 performs the image determining process on an in-vivo image of the subject 1 captured. The image display apparatus 74 is an example of the image display apparatus of the present invention, and performs the image determining process in the second stage without performing the image determining process in the first stage in the above-described image determining processes in the two stages. Specifically, the image display apparatus 74 obtains the in-vivo image group PG subjected to the image determining process in the first stage by the capsule endoscope 82 via the portable recording medium 5, and performs the image determining process in the second stage on each of the in-vivo images (that is, each of the in-vivo images on which the image determining process is performed in the first stage by the capsule endoscope 82) in the obtained in-vivo image group PG. Except for the above, the image display apparatus 74 has functions similar to those of the image display apparatus 4 of the first embodiment.

Figure 17:
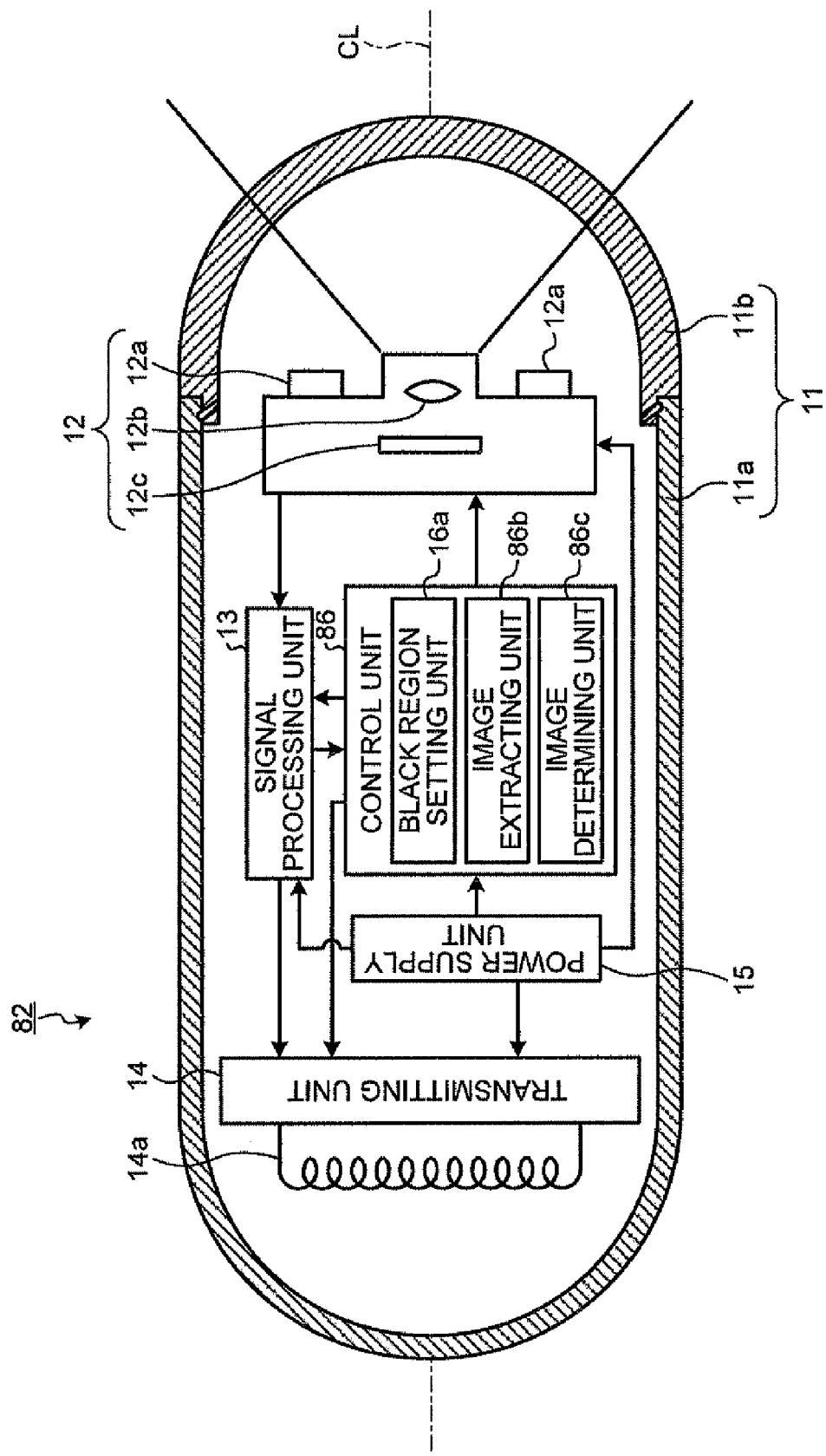
FIG. 17 is a schematic view showing a configuration example of a capsule endoscope in the fourth embodiment of the invention.

Next, the configuration of the capsule endoscope 82 as an example of the image pickup apparatus in the fourth embodiment of the present invention will be described in detail. FIG. 17 is a schematic view illustrating a configuration example of the capsule endoscope in the fourth embodiment of the invention. As shown in FIG. 17, the capsule endoscope 82 of the fourth embodiment has a control unit 86 in place of the control unit 16 of the capsule endoscope 2 of the first embodiment. The control unit 86 has an image extracting unit 86b for extracting a successive image group of in-vivo images captured by the imaging unit 12 and an image determining unit 86c for determining the influence of fluctuations in the power source voltage on each of the in-vivo images captured by the imaging unit 12. The other configuration is similar to that of the first embodiment, and the same reference numerals are designated to the same components.

The control unit 86 has the black region setting unit 16a and, further, has the image extracting unit 86b and the image determining unit 86c. The control unit 86 has the function similar to that of the control unit 16 of the capsule endoscope 2 in the first embodiment except for the functions of the image extracting unit 86b and the image determining unit 86c (the image determining process functions on in-vivo images). The control unit 86 controls the signal processing unit 13 and the transmitting unit 14 so as to wirelessly transmit an image signal including an in-vivo image subjected to the image determining process in the image determining unit 86c to the receiving device 3 outside the subject 1.

The image extracting unit 86b extracts a successive image group of images continuous only by the predetermined number of frames in time series from a series of images including an in-vivo image to be subjected to the image determining process of the image determining unit 86c. Concretely, the image extracting unit 86b sequentially obtains the in-vivo images captured by the imaging unit 12 from the signal processing unit 13. As a result, the image extracting unit 86b extracts a successive image group including the in-vivo image to be determined from the in-vivo image group captured by the imaging unit 12.

The successive image group extracted by the image extracting unit 86b may be a successive image group including the in-vivo image to be determined in the head frame, a successive image group in which in-vivo images of a predetermined number of frames continue before and after the in-vivo image to be determined, or a successive image group including the in-vivo image to be determined in the last frame.

The image determining unit 86c has an image determining process function substantially similar to that of the image determining unit 45c of the image display apparatus 4 of the first embodiment. Concretely, the image determining unit 86c calculates the number of 0-level pixels in the black regions C1 to C4 based on the signal levels of the black regions C1 to C4 in in-vivo images in the successive image group extracted by the image extracting unit 86b, and performs the image determining process on the in-vivo images using the calculated number of 0-level pixels (that is, the image determining process in the first stage by the image determining unit 45c). More concretely, the image determining unit 86c compares the average value of the numbers of 0-level pixels as the pixel information of the black regions C1 to C4 with a predetermined threshold. In the case where the average value of the numbers of 0-level pixels exceeds the preset threshold, the image determining unit 86c determines that the in-vivo image to be determined is an image influenced by fluctuations in the power source voltage. In the case where the average value of the numbers of 0-level pixels is equal to or less than the preset threshold, the image determining unit 86c determines that the in-vivo image to be determined is a stable image. The image determining unit 86c sequentially performs the image determining process on each of in-vivo images Pn (n=1, 2, 3, . . . ) captured by the imaging unit 12, inhibits output of an in-vivo image determined as an image influenced by fluctuations in the power source voltage by the image determining process, and permits output of an in-vivo image determined as a stable image. Like the image determining unit 45c in the foregoing first embodiment, the image determining unit 86c does not add an image output stop flag to an in-vivo image determined as a stable image but adds the image output stop flag to an in-vivo image determined as an image influenced by fluctuations in the power source voltage.

Figure 18:
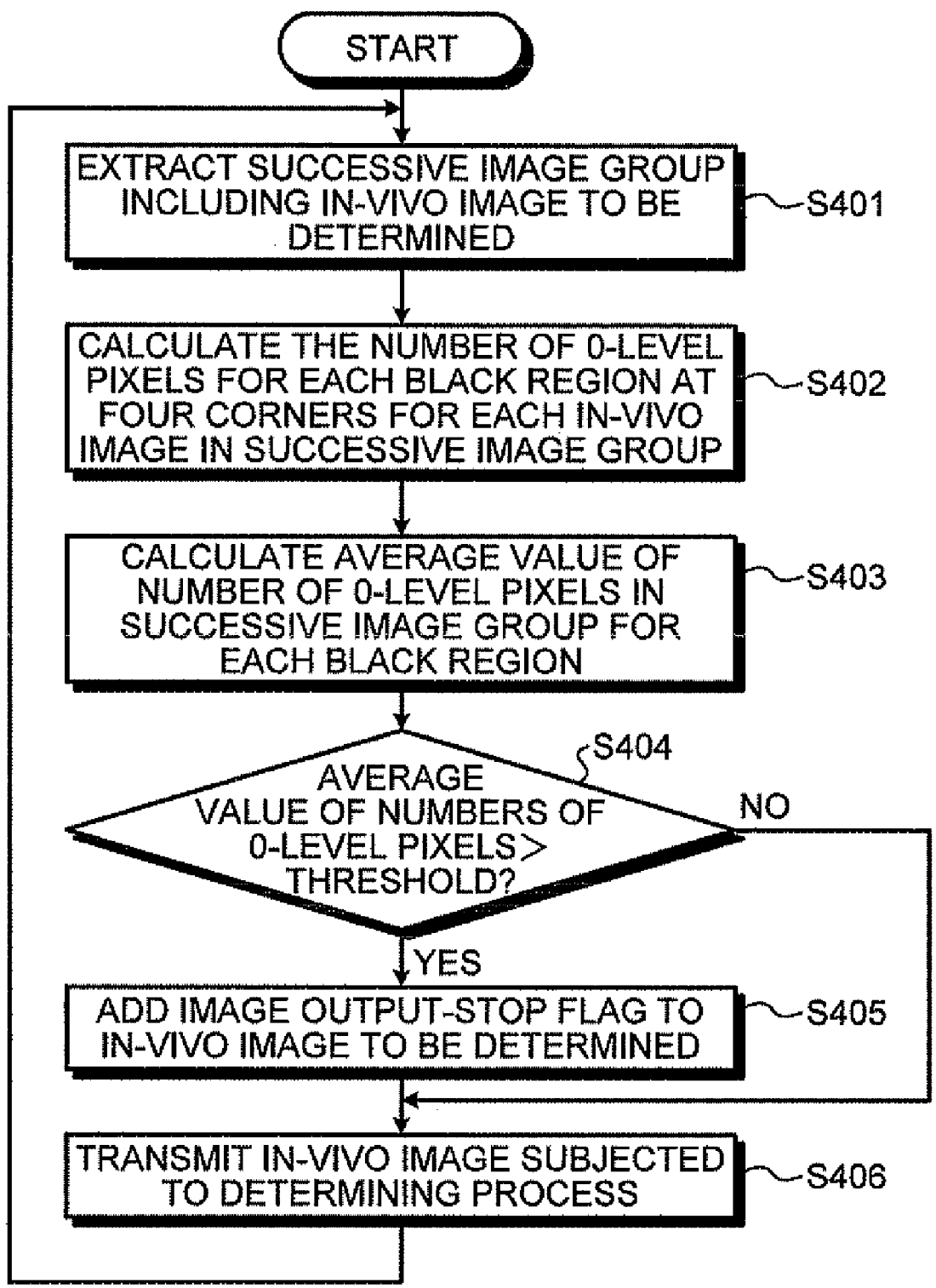
FIG. 18 is a flowchart illustrating a procedure of a control unit of a capsule endoscope for performing an image determining process on an in-vivo image by using the number of pixels of the level 0 in the black region.

Next, the operation of the capsule endoscope 82 in the fourth embodiment of the invention will be described. FIG. 18 is a flowchart illustrating a procedure of a control unit in a capsule endoscope for performing the image determining process on an in-vivo image by using the number of 0-level pixels in a black region. In the case where capturing of an in-vivo image of the subject 1 is started by the imaging unit 12, the control unit 86 of the capsule endoscope 82 performs the image determining process on each of in-vivo images $P_n$ (n=1, 2, 3, . . . ) by the imaging unit 12 with respect to an image influenced by consumption of power of the power supply unit 15 (concretely, an image influenced by fluctuations in the black reference level), and inhibits or permits output of each of the in-vivo images $P_n$ in accordance with the result of the image determining process.

As shown in FIG. 18, the control unit 86 extracts a successive image group including an in-vivo image $P_n$ to be determined from a group of in-vivo images sequentially taken by the imaging unit 12 (step S401). In this case, the image determining unit 86c determines the in-vivo image $P_n$ to be determined along the forward direction of the time series (the ascending order of the frame numbers "n") from the in-vivo image group taken by the imaging unit 12. The image extracting unit 86b extracts a successive image group of a predetermined number of frames (for example, three frames) including the in-vivo image $P_n$ to be determined by the image determining unit 86c from the signal processing unit 13.

Next, in a manner similar to the step S102 shown in FIG. 6, the control unit 86 calculates the number of 0-level pixels of the black regions C1 to C4 at four corners in each of the in-vivo images in the successive image group extracted in step S401 (step S402). In the step S402, like the image determining unit 45c in the first embodiment, the image determining unit 86c calculates the number of 0-level pixels in each of the black regions C1 to C4 in each of the in-vivo images included in the successive image group.

Subsequently, in a manner similar to the step S103 shown in FIG. 6, based on each of the numbers of 0-level pixels in the black regions C1 to C4 calculated for each of the in-vivo images in step S402, the control unit 86 calculates an average value of the numbers of the 0-level pixels in the successive image group on each of the black regions (step S403). In the step S403, like the image determining unit 45c in the first embodiment, the image determining unit 86c calculates the average value of the 0-level pixel numbers in the black region C1 in the successive image group, the average value of the 0-level pixel numbers in the black region C2, the average value of the 0-level pixel numbers in the black region C3, and the average value of the 0-level pixel numbers in the black region C4.

Next, like in the steps S104 and S105 shown in FIG. 6, the control unit 86 determines whether the average value of the 0-level pixel numbers in each of the black regions C1 to C4 calculated in the step S403 exceeds a predetermined threshold or not (step S404). In the case where the average value exceeds the predetermined threshold (Yes in step S404), it is determined that the in-vivo image $P_n$ to be determined is influenced by fluctuations in the power source voltage, and an image output stop flag is added to the in-vivo image $P_n$ to be determined (step S405). In steps S404 and S405, like the image determining unit 45c in the first embodiment, the image determining unit 86c determines the influence of fluctuations in the power source voltage on the in-vivo image $P_n$ to be determined based on a result of comparison between the average value of the numbers of 0-level pixels in each of the black regions C1 to C4 with the preset threshold, and adds an image output stop flag to the in-vivo image determined as an image influenced by fluctuations in the power source voltage. By adding the image output stop flag to an in-vivo image, the image determining unit 86c inhibits output of the in-vivo image influenced by fluctuations in the power source voltage.

After that, the control unit 86 controls the signal processing unit 13 and the transmitting unit 14 so as to wirelessly transmit the in-vivo image subjected to the image determining process of the image determining unit 86c to the outside (step S406). After that, the control unit 86 returns to the step S401 and repeats the processes in the step S401 and the subsequent steps. In the step S406, the control unit 86 makes the signal processing unit 13 generate an image signal including the in-vivo image subjected to the determining process, and makes the transmitting unit 14 wirelessly transmit the image signal.

On the other hands in the case where the average value of the 0-level pixel numbers in each of the black regions C1 to C4 is equal to or less than the predetermined threshold in the step S404 (No in step S404), the control unit 86 determines that the in-vivo image $P_n$ to be determined is an image which is not influenced by fluctuations in the power source voltage. Without adding the image output stop flag to the in-vivo image $P_n$ to be determined, the control unit 86 advances to step S406. In the step S404, like the image determining unit 45c in the first embodiment, in the case where the average value of the 0-level pixel numbers in each of the black regions C1 to C4 is equal to or less than the threshold value, the in-vivo image $P_n$ to be determined is determined as an image which is not influenced by fluctuations in the power source voltage by the image determining unit 86c. Without adding the image output stop flag to the in-vivo image, the image determining unit 86c permits output of the in-vivo image which is not influenced by fluctuations in the power source voltage.

The capsule endoscope 82 having such a control unit 86 sequentially performs the image determining operation on each of the in-vivo images $P_n$ (n=1, 2, 3, . . . ) captured by the imaging unit 12 by the image determining unit 86c. The capsule endoscope 82 sequentially wirelessly transmits, the in-vivo images $P_n$ subjected to the determining process and inhibited or permitted to be output by the image determining unit 86c to the receiving device 3 outside the subject 1 by the transmitting unit 14.

As described above, in the fourth embodiment of the present invention, the image determining process is performed on each of images on the side of the image pickup apparatus for capturing a desired image such as a in-vivo image of a subject, and the images subjected to the image determining process are transmitted to the outside (the receiving device side or the image display apparatus side). The other configuration is similar to that of the first embodiment. Consequently, in a manner substantially similar to the first embodiment, output of an image influenced by fluctuations in the black reference level can be easily stopped. As a result, the image pickup apparatus, the image display apparatus, and the image display system enjoying the effects similar to those of the first embodiment can be realized.

Fifth Embodiment

Next, a fifth embodiment of the present invention will be described. In the foregoing fourth embodiment, the influence of fluctuations in the power source voltage on each of in-vivo images is determined by using the numbers of 0-level pixels in the black regions C1 to C4. In the fifth embodiment, the influence of fluctuations in the power source voltage on each of in-vivo images is determined by using a variation value of the signal level in a black region in the beginning of the operation of the imaging unit.

Figure 19:
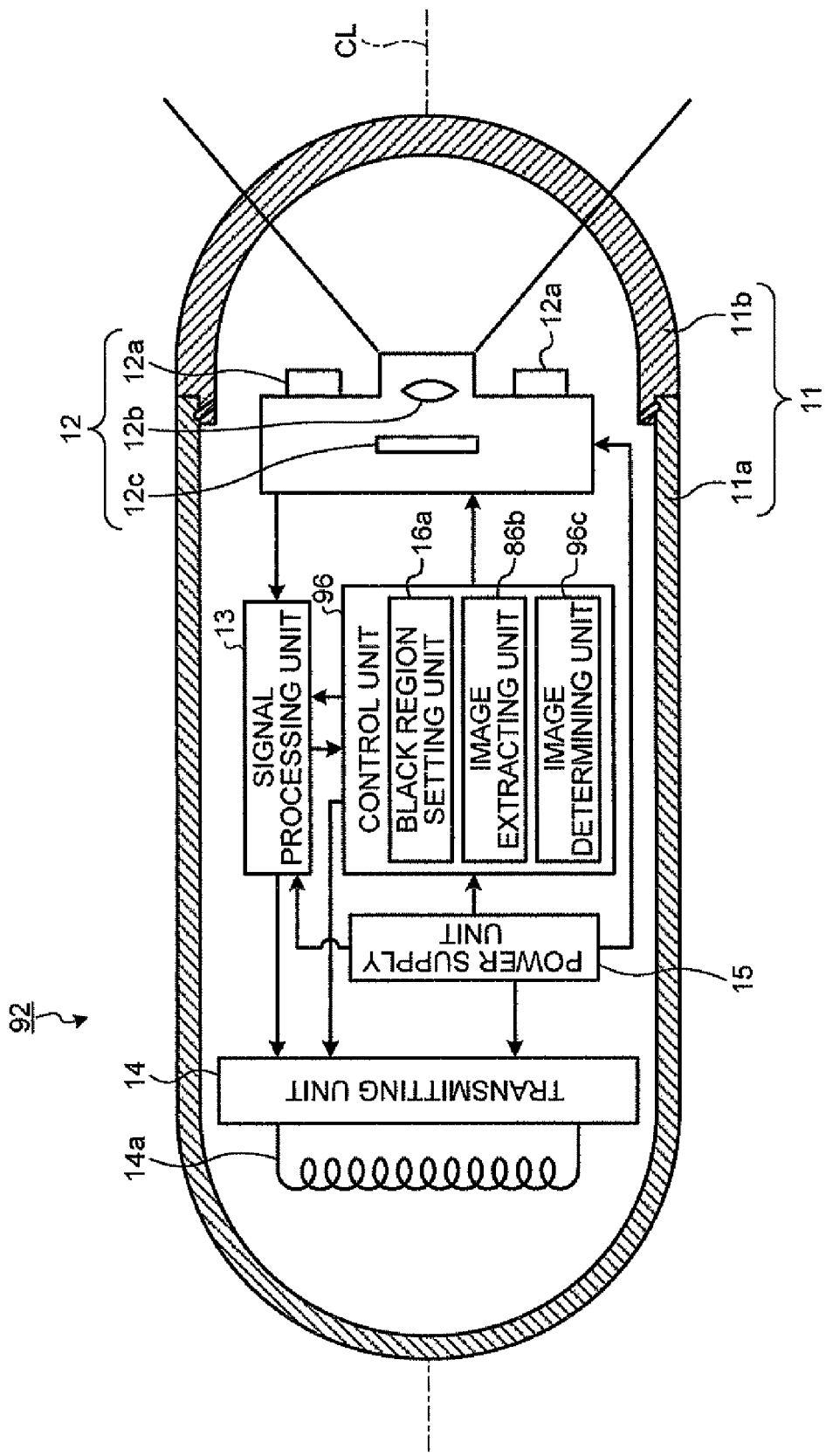
FIG. 19 is a block diagram schematically showing a configuration example of a capsule endoscope as an example of an image pickup apparatus as a fifth embodiment of the invention.

FIG. 19 is a block diagram schematically showing a configuration example of a capsule endoscope as an example of an image pickup apparatus in the fifth embodiment of the present invention. As shown in FIG. 19, a capsule endoscope 92 of the fifth embodiment has a control unit 96 in place of the control unit 86 of the capsule endoscope 82 in the fourth embodiment. The other configuration is similar to that of the fourth embodiment, and the same reference numerals are designated to the same components. An image display system of the fifth embodiment has the capsule endoscope 92 in place of the capsule endoscope 82 in the image display system (refer to FIG. 16) of the fourth embodiment.

The control unit 96 has an image determining unit 96c in place of the image determining unit 86c of the capsule endoscope 82 in the fourth embodiment. The control unit 96 has the function similar to that of the control unit 86 in the fourth embodiment except for the function of the image determining unit 96c. The control unit 96 controls the signal processing unit 13 and the transmitting unit 14 so as to wirelessly transmit an image signal including an in-vivo image in which the influence of fluctuations in the power source voltage is determined in the image determining unit 96c to the receiving device 3 outside the subject 1.

The image determining unit 96c has an image determining process function substantially similar to that of the image determining unit 55c of the image display apparatus 54 of the second embodiment. Concretely, the image determining unit 96c calculates a variation value of each of the average brightnesses in the black regions C1 to C4 based on the signal levels of the black regions C1 to C4 in in-vivo images in the successive image group extracted by the image extracting unit 86b, and performs the image determining process on the in-vivo images based on the calculated variation values of the average brightnesses (that is, the image determining process in the first stage by the image determining unit 55c).

The variation value of each of the average brightness in the black regions C1 to C4 is a variation value for each of the average brightnesses in the beginning of the operation of the capsule endoscope 92, and is an example of pixel information of the black region which changes due to fluctuations in the output of the power supply unit 15 for supplying power to the imaging unit 12. The image determining unit 96c sequentially performs the image determining process on each of in-vivo images $P_n$ (n=1, 2, 3, . . . ) by comparing a variation value of each of the average brightnesses as pixel information of the black regions C1 to C4 with a preset threshold. The image determining unit 96c inhibits output of an in-vivo image determined as an image influenced by fluctuations in the power source voltage by the image determining process, and permits output of an in-vivo image determined as a stable image which is not influenced by fluctuations in the power source voltage. Like the image determining unit 55c in the second embodiment, the image determining unit 96c does not add the image output stop flag to a stable in-vivo image which is not influenced by fluctuations in the power source voltage, but adds the image output stop flag to an in-vivo image determined as an image influenced by fluctuations in the power source voltage.

Figure 20:
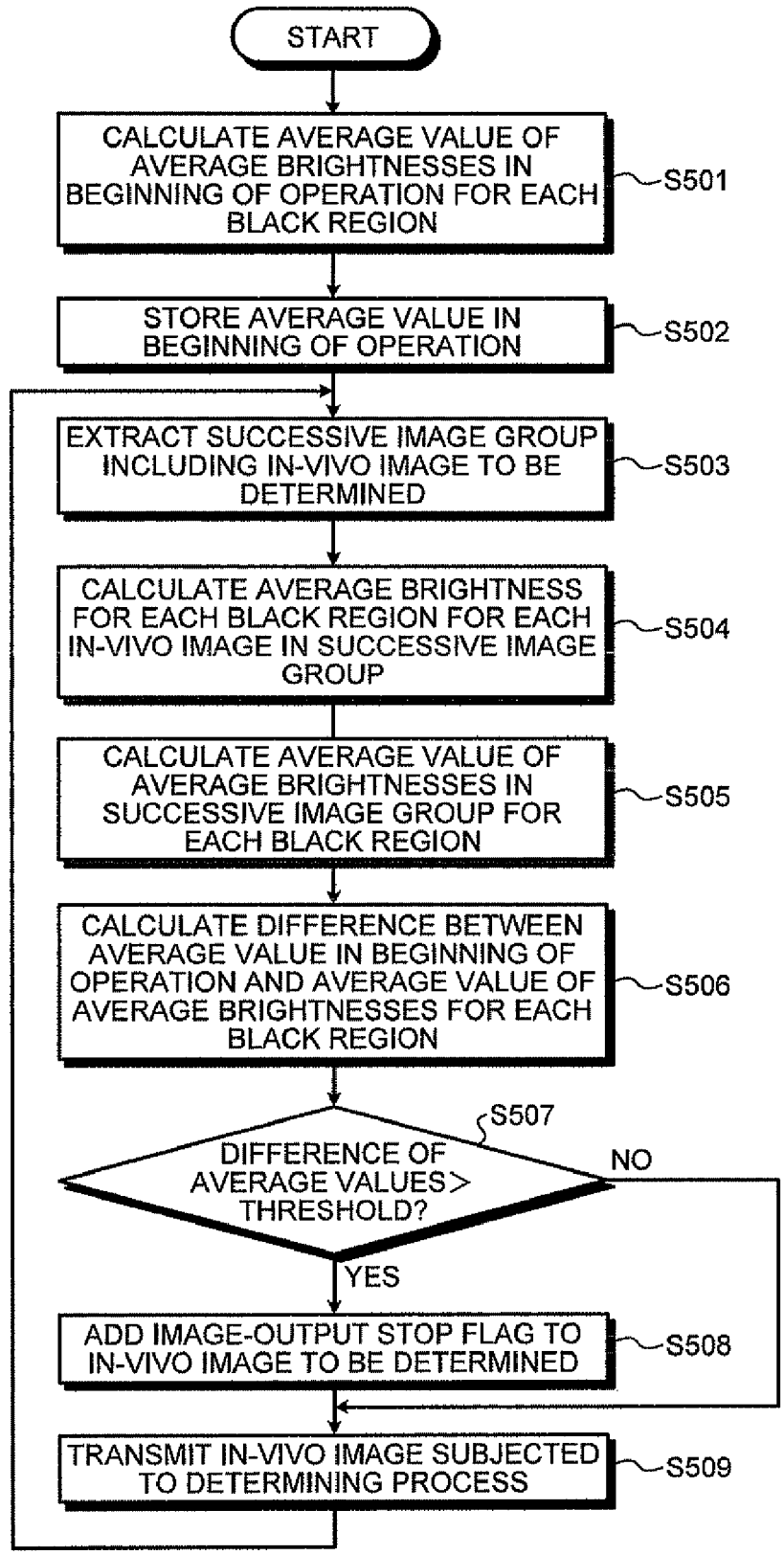
FIG. 20 is a flowchart illustrating a procedure of a control unit of a capsule endoscope for performing an image determining process on an in-vivo image using a variation value of average brightness in a black region in the beginning of operation.

Next, the operation of the capsule endoscope 92 in the fifth embodiment of the present invention will be described. FIG. 20 is a flowchart illustrating a procedure of a control unit in a capsule endoscope for performing the image determining process on an in-vivo image by using a variation value of average brightness in a black region in the beginning of the operation. In the case where capturing of an in-vivo image of the subject 1 is started by the imaging unit 12, the control unit 96 of the capsule endoscope 92 performs the image determining process on each of in-vivo images $P_n$ (n=1, 2, 3, . . . ) by the imaging unit 12 with respect to an image influenced by consumption of power of the power supply unit 15 (concretely, an image influenced by fluctuations in the black reference level), and inhibits or permits output of each of the in-vivo images $P_n$ in accordance with the result of the image determining process.

As shown in FIG. 20, first, the control unit 96 calculates an average value of average brightnesses in the beginning of the operation of the capsule endoscope 92 for each of the black regions (step S501). In the step S501, the image extracting unit 86b extracts a successive image group including predetermined number of frames (for example, three frames) including an in-vivo image $P_1$ in the first frame taken by the imaging unit 12 from the signal processing unit 13. The image determining unit 96c obtains a brightness level for each of the black regions in each of in-vivo images included in the extracted successive image group and, based on the obtained brightness levels, calculates the average brightnesses in the black regions C1 to C4 of each of the in-vivo images. The image determining unit 96c divides a value obtained by totaling the average brightnesses by black region by the number of frames in the successive image group, thereby calculating the average value of the average brightnesses in each of the black regions C1 to C4. The average value is an average value of average brightnesses in each of the black regions C1 to C4 in the beginning of the operation of the capsule endoscope 92.

Next, the control unit 96 stores the average value in the beginning of the operation calculated by black region in the step S501 into a RAM or the like of itself (step S502). In this case, the image determining unit 96c sets the average value in the beginning of the operation as a computation parameter used for an image determining process on an in-vivo image.

Subsequently, the control unit 96 extracts a successive image group including the in-vivo image $P_n$ to be determined from a group of in-vivo images sequentially taken by the imaging unit 12 (step S503). In this case, the image determining unit 96c determines the in-vivo image $P_n$ to be determined along the forward direction of the time series (ascending order of the frame numbers "n") from the in-vivo image group taken by the imaging unit 12. The image extracting unit 86b extracts a successive image group of a predetermined number of frames (for example, three frames) including the in-vivo image $P_n$ to be determined by the image determining unit 96c from the signal processing unit 13.

Next, in a manner similar to the step S204 shown in FIG. 11, the control unit 96 calculates the average brightnesses in the black regions C1 to C4 in each of the in-vivo images in the successive image group extracted in step S503 (step S504). In the step S504, like the image determining unit 55c in the second embodiment, the image determining unit 96c calculates the average brightness in each of the black regions C1 to C4 in each of the in-vivo images included in the successive image group.

Subsequently, in a manner similar to the step S205 shown in FIG. 11, based on each of the average brightnesses in the black regions C1 to C4 calculated for each of the in-vivo images in step S504, the control unit 96 calculates an average value of the average brightnesses in the successive image group on each of the black regions (step S505). In the step S505, like the image determining unit 55c in the second embodiment, the image determining unit 96c calculates the average value of the average brightnesses in the black region C1 in the successive image group, the average value of the average brightnesses in the black region C2, the average value of the average brightnesses in the black region C3, and the average value of the average brightnesses in the black region C4.

After that, like in the step S206 shown in FIG. 11, the control unit 96 calculates the difference between the average value in the beginning of the operation calculated in the step S501 and the average value of average brightnesses for each of the black regions calculated in the step S505 (step S506). In the step S506, like the image determining unit 55c in the second embodiment, the image determining unit 96c calculates the difference between the average value in the beginning of the operation and the average value of the average brightnesses in the black region C1 in the successive image group, the difference between the average value in the beginning of the operation and the average value of the average brightnesses in the black region C2 in the successive image group, the difference between the average value in the beginning of the operation and the average value of the average brightnesses in the black region C3 in the successive image group, and the difference between the average value in the beginning of the operation and the average value of the average brightnesses in the black region C4 in the successive image group. The difference between the average value in the beginning of the operation and the average value of the average brightnesses in each of the black regions C1 to C4 corresponds to a variation value (transition) of each of the average brightnesses in the black regions C1 to C4 in the beginning of the operation of the capsule endoscope 92.

Next, like in the steps S207 and S208 shown in FIG. 11, the control unit 96 determines whether the difference of the average values calculated in step S506 exceeds a predetermined threshold or not (step S507). In the case where the difference exceeds the predetermined threshold (Yes in step S507), it is determined that the in-vivo image $P_n$ to be determined is influenced by fluctuations in the power source voltage, and an image output stop flag is added to the in-vivo image $P_n$ to be determined (step S508. In steps S507 and S508, like the image determining unit 55c in the second embodiment, the image determining unit 96c compares the difference between the average value in the beginning of the operation and the average value of the average brightnesses in the black regions C1 to C4, that is, a variation value of the average brightnesses in the black regions C1 to C4 in the beginning of the operation with a preset threshold. Based on a result of the comparison, the image determining unit 96c determines the in-vivo image $P_n$ to be determined. The image determining unit 96c adds the image output stop flag to the in-vivo image which is determined as an image influenced by fluctuations in the power source voltage. With the image output stop flag, output of the in-vivo image determined as an image influenced by fluctuations in the power source voltage is inhibited.

After that, the control unit 96 controls the signal processing unit 13 and the transmitting unit 14 so as to wirelessly transmit the in-vivo image subjected to the image determining process of the image determining unit 96c to the outside (step S509). After that, the control unit 96 returns to the step S503 and repeats the procedures in the step S503 and the subsequent steps. In the step S509, the control unit 96 makes the signal processing unit 13 generate an image signal including the in-vivo image subjected to the determining process, and makes the transmitting unit 14 wirelessly transmit the image signal.

On the other hand, in the case where the difference between the average value in the beginning of the operation and the average value of the average brightnesses in each of the black regions C1 to C4 is equal to or less than the predetermined threshold in the step S507 (No in step S507), the control unit 96 determines that the in-vivo image $P_n$ to be determined is an image which is not influenced by fluctuations in the power source voltage. Without adding the image output stop flag to the in-vivo image $P_n$ to be determined, the control unit 96 advances to step S509. In the step S507, like the image determining unit 55c in the second embodiment, in the case where the difference between the average value in the beginning of the operation and the average value of the average brightnesses in each of the black regions C1 to C4, that is, the variation value of the average brightnesses of each of the black regions C1 to C4 in the beginning of the operation is equal to or less than the threshold, the image determining unit 96c determines that the in-vivo image $P_n$ to be determined is not influenced by fluctuations in the power source voltage. In this case, without adding the image output stop flag to the in-vivo image determined as an image which is not influenced by fluctuations in the power source voltage, the image determining unit 96c permits output of the in-vivo image determined as an image which is not influenced by fluctuations in the power source voltage.

The capsule endoscope 92 having such a control unit 96 sequentially performs the image determining operation on each of the in-vivo images $P_n$ (n=1, 2, 3, . . . ) captured by the imaging unit 12 by the image determining unit 96c. The capsule endoscope 92 sequentially, wirelessly transmits the in-vivo images $P_n$ subjected to the determining process and inhibited or permitted to be output by the image determining unit 96c to the receiving device 3 outside the subject 1 by the transmitting unit 14.

As described above, in the fifth embodiment of the present invention, the image determining unit calculates a variation value of the average brightness level of a black region in the beginning of the operation of the imaging unit based on a signal level of the black region, and performs the image determining process on each of images by using the calculated variation value of the average brightness level of the black region. The other configuration is similar to that of the fourth embodiment. Consequently, in a manner similar to the fourth embodiment, output (display) of an image influenced by fluctuations in the black reference level can be easily stopped. As a result, the image pickup apparatus, the image display apparatus, and the image display system enjoying the effects similar to those of the fourth embodiment can be realized.

Sixth Embodiment

Next, a sixth embodiment of the present invention will be described. In the foregoing fourth embodiment, the influence of fluctuations in the power source voltage on each of in-vivo images is determined by using the number of 0-level pixels in the black regions C1 to C4. In the sixth embodiment, the influence of fluctuations in the power source voltage on each of in-vivo images is determined by using a signal level difference among a plurality of black regions in an in-vivo image to be determined.

Figure 21:
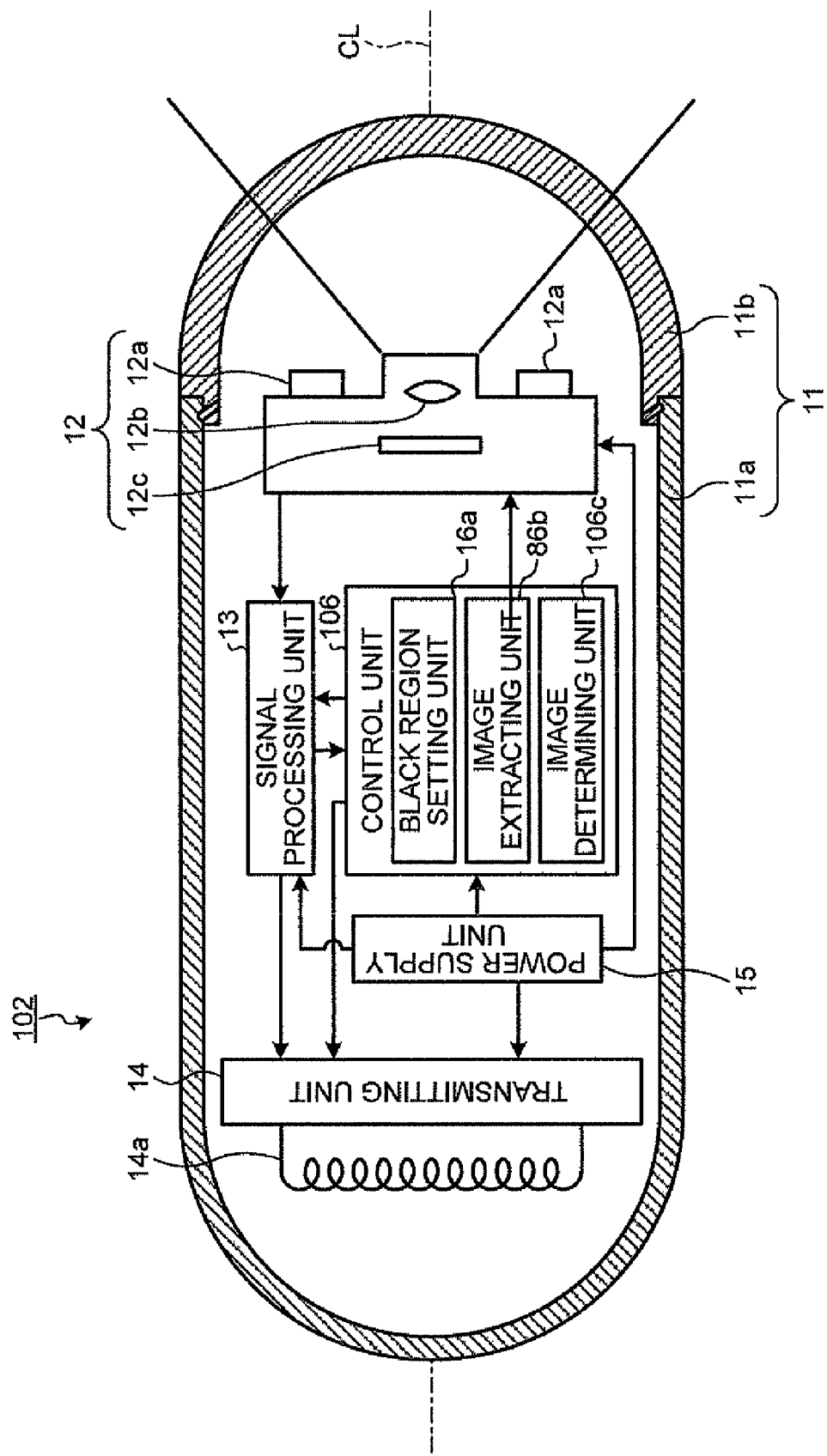
FIG. 21 is a block diagram schematically showing a configuration example of a capsule endoscope as an example of an image pickup apparatus as a sixth embodiment of the invention.

FIG. 21 is a block diagram schematically showing a configuration example of a capsule endoscope as an example of an image pickup apparatus in the sixth embodiment of the present invention. As shown in FIG. 21, a capsule endoscope 102 of the sixth embodiment has a control unit 106 in place of the control unit 86 of the capsule endoscope 82 in the fourth embodiment. The other configuration is similar to that of the fourth embodiment, and the same reference numerals are designated to the same components. An image display system of the sixth embodiment has the capsule endoscope 102 in place of the capsule endoscope 82 in the image display system (refer to FIG. 16) of the fourth embodiment.

The control unit 106 has an image determining unit 106c in place of the image determining unit 86c of the capsule endoscope 82 in the fourth embodiment. The control unit 106 has the function similar to that of the control unit 86 in the fourth embodiment except for the function of the image determining unit 106c. The control unit 106 controls the signal processing unit 13 and the transmitting unit 14 so as to wirelessly transmit, an image signal including an in-vivo image determined by the image determining unit 106c to the receiving device 3 outside the subject 1.

The image determining unit 106c has an image determining process function substantially similar to that of the image determining unit 65c of the image display apparatus 64 of the third embodiment. Concretely, the image determining unit 106c calculates a brightness level difference among the black regions C1 to C4 in each of the in-vivo images based on the signal levels of the black regions C1 to C4 in in-vivo images in the successive image group extracted by the image extracting unit 86b, and performs the image determining process on the in-vivo images using the calculated brightness level difference among the black regions C1 to C4 (that is, the image determining process in the first stage by the image determining unit 65c).

As described above, the brightness level difference among the black regions C1 to C4 is a brightness level difference between a pair of black regions in the same in-vivo image, and is an example of pixel information of the black region which changes due to fluctuations in the output of the power supply unit 15 for supplying power to the imaging unit 12. The image determining unit 106c sequentially performs the image determining process on each of in-vivo images $P_n$ (n=1, 2, 3, ...) by comparing the brightness level difference between a pair of black regions as pixel information of the black regions C1 to C4 with a preset threshold. The image determining unit 106c inhibits output of an in-vivo image determined as an image influenced by fluctuations in the power source voltage by the image determining process, and permits output of an in-vivo image determined as a stable image which is not influenced by fluctuations in the power source voltage. Like the image determining unit 65c in the third embodiment, the image determining unit 106c does not add the image output stop flag to an in-vivo image determined as a stable image which is not influenced by fluctuations in the power source voltage, but adds the image output stop flag to an in-vivo image determined as an image influenced by fluctuations in the power source voltage.

Figure 22:
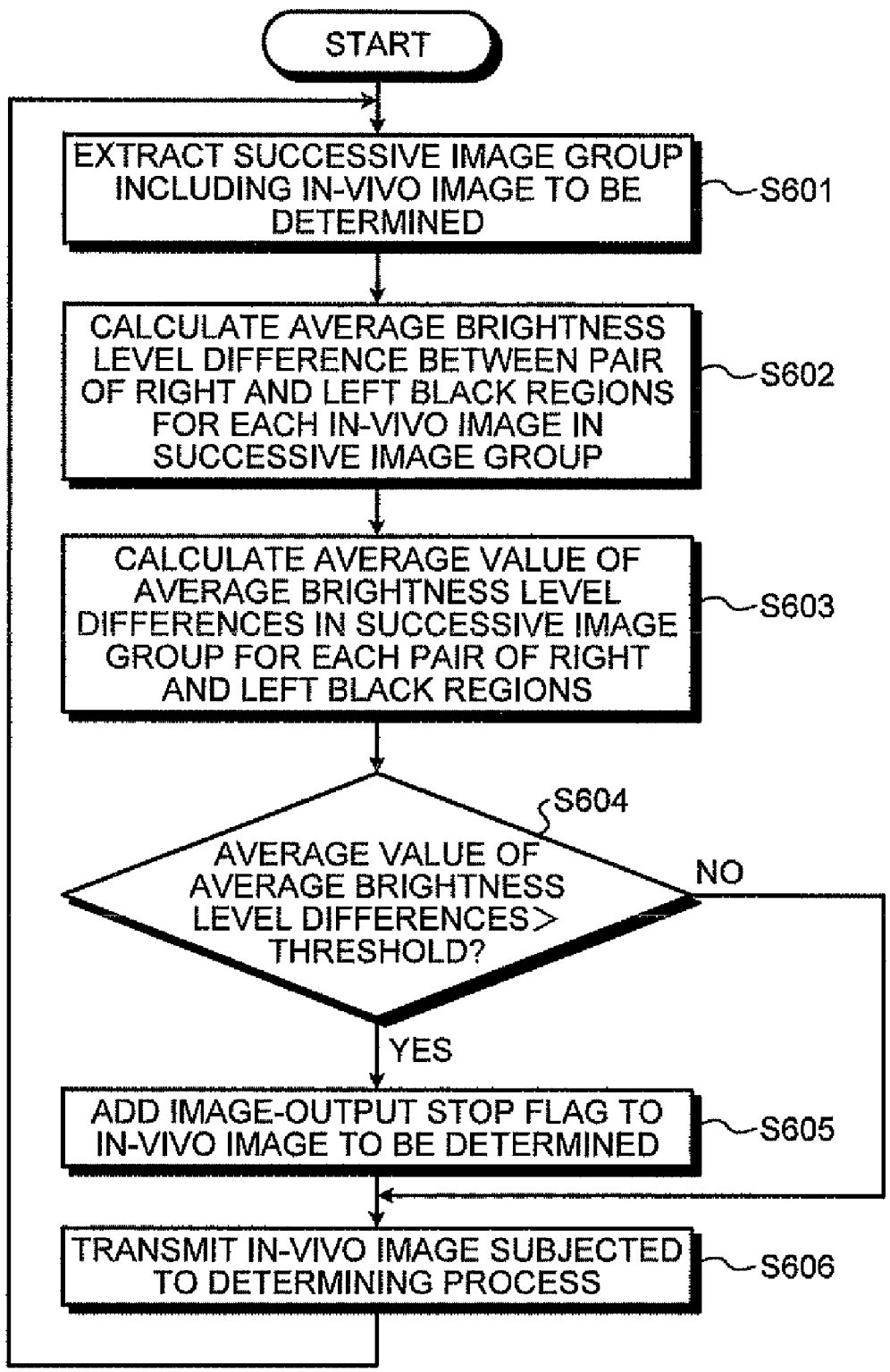
FIG. 22 is a flowchart illustrating a procedure of a control unit of a capsule endoscope for performing an image determining process on an in-vivo image by using a brightness level difference between a pair of black regions in a single in-vivo image.

Next, the operation of the capsule endoscope 102 in the sixth embodiment of the present invention will be described. FIG. 22 is a flowchart illustrating a procedure of a control unit in a capsule endoscope for performing the image determining process on an in-vivo image by using the brightness level difference between a pair of black regions in the same in-vivo image. In the case where capturing of an in-vivo image of the subject 1 is started by the imaging unit 12, the control unit 106 of the capsule endoscope 102 performs the image determining process on each of in-vivo images $P_n$ (n=1, 2, 3, ...) by the imaging unit 12 with respect to an image influenced by consumption of power of the power supply unit 15 (concretely, an image influenced by fluctuations in the black reference level), and inhibits or permits output of each of the in-vivo images $P_n$ in accordance with the result of the image determining process.

As shown in FIG. 22, the control unit 106 extracts a successive image group including an in-vivo image $P_n$ to be determined from a group of in-vivo images sequentially captured by the imaging unit 12 (step S601). In this case, the image determining unit 106c determines the in-vivo image $P_n$ to be determined along the forward direction of the time series (ascending order of the frame numbers "n") from the in-vivo image group taken by the imaging unit 12. The image extracting unit 86b extracts a successive image group of a predetermined number of frames (for example, three frames) including the in-vivo image $P_n$ to be determined by the image determining unit 106c from the signal processing unit 13.

Next, in a manner similar to the step S302 shown in FIG. 14, the control unit 106 calculates the average brightness level difference between a pair of right and left black regions in each of the in-vivo images in the successive image group extracted in step S601 (step S602). In the step S602, like the image determining unit 65c in the third embodiment, the image determining unit 106c calculates the average brightness level difference between a pair of right and left black regions C1 and C2 on the upper side and the average brightness level difference between a pair of right and left black regions C3 and C4 on the lower side in each of the in-vivo images included in the successive image group.

Subsequently, in a manner similar to the step S303 shown in FIG. 14, the control unit 106 calculates an average value of the average brightness level difference in the successive image group every pair of right and left black regions by using the average brightness level difference between the pair of right and left black regions C1 and C2 on the upper side and the average brightness level difference between the pair of right and left black regions C3 and C4 on the lower side in each of the in-vivo images calculated in the step S602 (step S603). In the step S603, like the image determining unit 65c in the third embodiment, the image determining unit 106c calculates the average value of the average brightness level difference between the pair of right and left black regions C1 and C2 on the upper side and the average value of the average brightness level difference between the pair of right and left black regions C3 and C4 on the lower side in the successive image group.

After that, like in the steps S304 and S305 shown in FIG. 14, the control unit 106 determines whether the average value of the average brightness level differences calculated in the step S603 exceeds a predetermined threshold or not (step S604). In the case where the average value exceeds the predetermined threshold (Yes in step S604), the control unit 106 determines that the in-vivo image $P_n$ to be determined is an image influenced by fluctuations in the power source voltage, and adds an image output stop flag to the in-vivo image $P_n$ to be determined (step S605). In the steps S604 and S605, like the image determining unit 65c in the third embodiment, the image determining unit 106c compares the average value of the average brightness level differences in the pair of right and left black regions C1 and C2 on the upper side in the successive image group with a preset threshold. Further, the image determining unit 106c compares the average value of the average brightness level differences in the pair of right and left black regions C3 and C4 on the lower side in the successive image group with a preset threshold. Based on a result of the comparing process, the image determining unit 106c determines the in-vivo image $P_n$ to be determined. The image determining unit 106c adds the image output stop flag to the in-vivo image which is determined as an image influenced by fluctuations in the power source voltage. With the image output stop flag, output of the in-vivo image determined as an image influenced by fluctuations in the power source voltage is inhibited.

After that, the control unit 106 controls the signal processing unit 13 and the transmitting unit 14 so as to wirelessly transmit the in-vivo image subjected to the image determining process of the image determining unit 106c to the outside (step S606). After that, the control unit 106 returns to the step S601 and repeats the procedures in the step S601 and the subsequent steps. In the step S606, the control unit 106 makes the signal processing unit 13 generate an image signal including the in-vivo image subjected to the determining process, and makes the transmitting unit 14 wirelessly transmit the image signal.

On the other hand, in the step S604, in the case where each of the average value of the average brightness level differences in the pair of right and left black regions C1 and C2 on the upper side and the average value of the average brightness level differences in the pair of right and left black regions C3 and C4 on the lower side is equal to or less than the predetermined threshold (No in step S604), the control unit 106 determines that the in-vivo image $P_n$ to be determined is an image which is not influenced by fluctuation in the power source voltage. The control unit 106 advances to step S606 without adding the image output stop flag to the in-vivo image $P_n$ to be determined. In the step S604, like the image determining unit 65c in the third embodiment, in the case where each of the average value of the average brightness level differences in the pair of right and left black regions C1 and C2 on the upper side and the average value of the average brightness level differences in the pair of right and left black regions C3 and C4 on the lower side is equal to or less than the threshold, the image determining unit 106c determines that the in-vivo image $P_n$ to be determined is not influenced by fluctuations in the power source voltage. In this case, without adding the image output stop flag to the in-vivo image determined as an image which is not influenced by fluctuations in the power source voltage, the image determining unit 106c permits output of the in-vivo image.

The capsule endoscope 102 having such a control unit 106 sequentially performs the image determining operation on each of the in-vivo images $P_n$ (n=1, 2, 3, . . . ) captured by the imaging unit 12 by the image determining unit 106c. The capsule endoscope 102 sequentially, wirelessly transmits the in-vivo images $P_n$ subjected to the determining process and inhibited or permitted to be output by the image determining unit 106c to the receiving device 3 outside the subject 1 by the transmitting unit 14.

As described above, in the sixth embodiment of the present invention, the image determining unit calculates the average value of brightness level differences among a plurality of black regions in the same image based on the signal levels of the black regions and, using the calculated average value of the brightness level differences, performs the image determining process on each of the images. The other configuration is similar to that of the fourth embodiment. Consequently, in a manner similar to the fourth embodiment, output (display) of an image determined as an image influenced by fluctuations in the power source voltage due to fluctuations in the black reference level can be easily stopped. As a result, the image pickup apparatus, the image display apparatus, and the image display system enjoying the effects similar to those of the fourth embodiment can be realized.

Since the image determining process is performed on images by using the brightness level differences among the black regions in the same image, the influence on an image caused by bias of the black reference level occurring in an image with fluctuations in the power source voltage of the imaging unit (consumption of the power source) can be directly determined. As a result, it is unnecessary to perform the image determining process in two or more stages on each of the images. Output of an image influenced by fluctuations in the power source voltage can be stopped reliably by the image determining process in the first stage.

In the first and fourth embodiments of the present invention, the image determining process is performed using the number of 0-level pixels in a black region which is set in the effective pixel region of the solid-state imaging device (the number of pixels in the black region having a brightness level lower than that in the case where there are no fluctuations in output of the power supply). However, the invention is not limited to the embodiments. The image determining process may be performed using a minimum brightness level in the black region.

Concretely, in the step S102, the image determining unit 45c in the first embodiment calculates the minimum brightness level in each of the black regions C1 to C4 for each of the in-vivo images in the successive image group extracted by the image extracting unit 45b in place of calculating the number of 0-level pixels in the black region. In the step S103, the image determining unit 45c calculates the average value of the minimum brightness levels in each of the black regions C1 to C4 in the successive image group in place of calculating the average value of the numbers of 0-level pixels. In the step S104, the image determining unit 45c compares the average value of minimum brightness levels of the black regions C1 to C4 with the preset threshold in place of comparing the average value of the numbers of 0-level pixels with the preset threshold. In the case where at least one of average values of the minimum brightness levels is less than the preset threshold, the image determining unit 45c determines that an in-vivo image to be determined is influenced by fluctuations in the power source voltage. In the case where each of average values of the minimum brightness levels is equal to or larger than the preset threshold, the image determining unit 45c determines that an in-vivo image to be determined is not influenced by fluctuations in the power source voltage. The image determining unit 45c may add the image output stop flag to an in-vivo image determined as an image influenced by fluctuations in the power source voltage by the image determining process using the minimum brightness level in the black regions.

Similarly, in the step S402, the image determining unit 86c in the fourth embodiment calculates the minimum brightness level in each of the black regions C1 to C4 for each of the in-vivo images in the successive image group extracted by the image extracting unit 86b in place of calculating the number of 0-level pixels in the black region. In the step S403, the image determining unit 86c calculates the average value of the minimum brightness levels in each of the black regions C1 to C4 in the successive image group in place of calculating the average value of the numbers of 0-level pixels. In the step S404, the image determining unit 86c compares the average value of minimum brightness levels of the black regions C1 to C4 with the preset threshold in place of comparing the average value of the numbers of 0-level pixels with the preset threshold. In the case where at least one of average values of the minimum brightness levels is less than the preset threshold, the image determining unit 86c determines that an in-vivo image to be determined is influenced by fluctuations in the power source voltage. In the case where each of average values of the minimum brightness levels is equal to or larger than the preset threshold, the image determining unit 86c determines that an in-vivo image to be determined is not influenced by fluctuations in the power source voltage. The image determining unit 86c may add the image output stop flag to an in-vivo image determined as an image influenced by fluctuations in the power source voltage by the image determining process using the minimum brightness level in the black regions.

In the first to sixth embodiments of the present invention, the capsule endoscopes for capturing an in-vivo image of a subject have been described as an example of the image pickup apparatus. The invention is not limited to the capsule endoscope. The image pickup apparatus of the present invention may be a digital camera or a digital video camera having an image transmitting function, or a portable information terminal such as a cellular phone or a PDA having an imaging function and a communication function. More specifically, the image pickup apparatus of the present invention may be any apparatus as long as it has an imaging function of capturing one or more images of a subject and a communication function of transmitting the captured image to the outside (for example, the side of a receiving device or the side of an image display apparatus outside of the image pickup apparatus). The image pickup apparatus of the present invention may wirelessly transmit an image to the outside communication as described in the capsule endoscope example, or by wired communication using a cable or the like.

In the first to third embodiments of the present invention, the image determining process is performed in the image display apparatus of the invention. In the fourth to sixth embodiments of the invention, the image determining process is performed by the image pickup apparatus of the present invention (for example, the capsule endoscope). The invention is not limited to the arrangement. The image determining process may be performed by a receiving device (for example, the receiving device 3) for receiving an image from the image pickup apparatus such as a capsule endoscope. In this case, the receiving device of the present invention may be provided with the image extracting unit and the image determining unit illustrated in any of the first to sixth embodiments and determine each of images in a series of images received from the image pickup apparatus by the image determining unit.

Further, in the first to sixth embodiments of the present invention, an in-vivo image captured by the capsule endoscope is displayed on the image display apparatus. The invention however is not limited to the configuration. It is also possible to provide a display unit for the receiving device for receiving an in-vivo image from the capsule endoscope and sequentially display in-vivo images on the display unit of the receiving device. In this case, the receiving device may have the image determining process function in one stage or two stages like the image display apparatuses in the first to third embodiments, display no in-vivo image determined as an image influenced by fluctuations in the power source voltage by the image determining process but display an in-vivo image determined as an image which is not influenced by fluctuations in the power source voltage.

In the first to sixth embodiments, the image determining process in two stages is performed by the image pickup apparatus or the image display apparatus. The invention is not limited to the configuration, the image determining process in the first stage may be performed on each of images captured by the image pickup apparatus and, by the image determining process in the first stage, inhibition or permission of output of each of the images may be determined. In short, the image determining process in the second stage may not be performed.

Further, in the fourth to sixth embodiments of the present invention, the image output stop flag is added to an in-vivo image determined as an image influenced by fluctuations in the power source voltage by the image determining unit of the capsule endoscope. The invention is not limited to the configuration. The image pickup apparatus such as the capsule endoscope may not transmit an image determined as an image influenced by fluctuations in the power source voltage by the image determining unit to the external receiving device or image display apparatus but may transmit only an image determined as an image which is not influenced by fluctuations in the power source voltage by the image determining unit to the external receiving device or image display apparatus. In this case, the image output stop flag may not be added to the image determined as an image influenced by fluctuations in the power source voltage.

In the first to sixth embodiments of the present invention, image data is transmitted from the receiving device to the image display apparatus via a portable recording medium. However, the invention is not limited to the arrangement. The receiving device of the present invention may transmit image data received from the image pickup apparatus to the image display apparatus by wireless communication or wired communication without using the portable recording medium.

Further, in the fourth to sixth embodiments of the invention, the image determining process in the first stage is performed by the image determining unit in the capsule endoscope, and the image determining process in the second stage is performed by the image display apparatus. However, the invention is not limited to the configuration, the image determining process in two stages may be performed by the image determining unit in the image pickup apparatus such as the capsule endoscope.

In the first to sixth embodiments of the invention, black regions are set at four corners of the effective pixel region in the solid-state imaging device. However, the invention is not limited to the configuration. The black regions contributing to the image determining process may be set in any pixel regions other than the four corners (for example, a peripheral portion in the effective pixel region) as long as they are in the effective pixel region of the solid-state imaging device. The black region may be any region where optical rays do not reach formed by one or more pixels in the effective pixel region.

Further, in the first to sixth embodiments of the present invention, the black regions are set in the effective pixel region of the solid-state imaging device by the black region setting unit 16a. The invention is not limited to the configuration. In the case where black regions cannot be set in the effective pixel region, an optical black region in the solid-state imaging device may be used in place of the black region.

In the first to third embodiments of the present invention, at the time of loading an in-vivo image group PG of the subject 1 from the portable recording medium 5, the image determining process is performed on each of the in-vivo images in the in-vivo image group PG. However, the invention is not limited to the configuration. It is also possible to store the in-vivo image group PG loaded from the portable recording medium 5 into the storage unit 44 and, after that, perform the image determining process on each of the in-vivo images included in the in-vivo image group PG in the storage unit 44.

Further, in the first, second, fourth, and fifth embodiments of the invention, the four black regions C1 to C4 in the effective pixel region are used for the image determining process on an in-vivo image. The invention is not limited to the case. The image determining process on an in-vivo image may be performed using at least one of the four black regions C1 to C4 (for example, only the black region C1).

According to the present invention, the imaging unit has a black region where optical rays do not reach in an effective pixel region contributing to image capture. The imaging unit captures an image by photoelectrically converting light information received via the effective pixel region, and detects signal level of the black region. The image determining unit performs an image determining process on each of the images by calculating pixel information of the black region which changes as output of a power source for supplying power to the imaging unit fluctuates based on the signal level of the black region in each of images captured by the imaging unit, and comparing the calculated pixel information with a predetermined threshold, and inhibits output of the image determined as the image influenced by fluctuations in the power source voltage by the image determining process. Thus, output of the image data influenced by fluctuations in the power source voltage, that is, image data influenced by fluctuations in the black reference level can be easily stopped. As a result, an effect that the invention can realize the image pickup apparatus capable of providing stable images, not an image influenced by fluctuations in the power source voltage, to the user is produced.

According to the present invention, the image obtaining unit obtains a series of images captured by the imaging unit having a black region where optical rays do not reach in an effective pixel region contributing to image capture and including a signal level of the black region in each of the images. The image determining unit performs an image determining process on each of the images by calculating pixel information of the black region which changes due to fluctuations in output of a power source for supplying power to the imaging unit based on the signal level of the black region in each of the images included in the series of images, and comparing the calculated pixel information with a threshold. The image determining unit inhibits output of an image determined as an image influenced by fluctuations in the power source voltage by the image determining process. The display control unit displays the series of images except for the image inhibited to be output by the image determining unit on the display unit. Thus, output of the image data influenced by fluctuations in the power source voltage, that is, image data influenced by fluctuations in the black reference level can be easily stopped. As a result, an effect that the invention can realize the image display apparatus capable of providing stable images, not an image influenced by fluctuations in the power source voltage, to the user is produced.

According to the present invention, the imaging unit has a black region where optical rays do not reach, in the effective pixel region contributing to image capture. The imaging unit captures an image by photoelectrically converting light information received via the effective pixel region and detects signal level of the black region. The image determining unit performs an image determining process on each of the images by calculating pixel information of the black region that changes due to fluctuations in the output of a power source for supplying power to the imaging unit based on the signal level of the black region in each of images included in the series of images and comparing the calculated pixel information with a threshold. The image determining unit inhibits output of the image determined as an image influenced by fluctuations in the power source voltage by the image determining process. The display control unit displays, on the display unit, the series of images except for the image inhibited to be output by the image determining unit. Thus, output of the image data influenced by fluctuations in the power source voltage, that is, image data influenced by fluctuations in the black reference level can be easily stopped. As a result, an effect that the invention can realize the image display system capable of providing stable images, not an image influenced by fluctuations in the power source voltage, to the user is produced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display apparatus comprising:
   an image obtaining unit for obtaining a series of images captured by an imaging unit having a black region where optical rays do not reach in a pixel region on an imaging device and including a signal level of the black region in each of the images, at least some of the series of images being obtained where there is a fluctuation in output of a power source supplied to the imaging unit;
   a display unit capable of displaying the series of images;
   an image determining unit for performing an image determining process on each of the images by calculating pixel information of the black region based on the signal level of the black region in each of the images included in the series of images and by comparing the calculated pixel information with a predetermined threshold, and inhibiting output of an image based on a result of determination of the image determining process, the pixel information of the black region being a number of low-brightness-level pixels in the black region, each of the low-brightness-level pixels having a brightness level lower than that of pixels in the black region in the case where there is no fluctuation in output of the power source supplied to the imaging unit; and
   a display control unit for displaying the series of images except for the image inhibited to be output by the image determining unit on the display unit.

2. The image display apparatus according to claim 1, further comprising an image extracting unit for extracting a successive image group including an image to be subjected to an image determining process of the image determining unit from the series of images,
   wherein the image determining unit calculates an average value of the low-brightness-level pixel numbers of the black region based on the signal levels of the black regions of the images included in the successive image group and, in the case where the calculated average value of the low-brightness-level pixel numbers is equal to or more than a predetermined threshold, inhibits output of the image.

3. The image display apparatus according to claim 1, wherein the pixel information of the black region is a minimum brightness level of the black region.

4. The image display apparatus according to claim 3, further comprising an image extracting unit for extracting a successive image group including an image to be subjected to an image determining process of the image determining unit from the series of images, wherein the image determining unit calculates an average value of minimum brightness levels of the black regions based on the signal levels of the black regions of the images included in the successive image group and, in the case where the calculated average value of the minimum brightness levels is equal to or less than a predetermined threshold, inhibits output of the image.

5. The image display apparatus according to claim 1, wherein the image determining unit adds an image output stop flag to the image which is inhibited to be output.

6. The image display apparatus according to claim 5, wherein the image determining unit determines whether or not there is an image to which the image output stop flag is not added in a frame after the image to which the image output stop flag is added in the series of images, in the case where there is an image to which the image output stop flag is not added, deletes the image output stop flag added to the image in the frame before the image to which the image output stop flag is not added to cancel inhibition of output of the image, and the display control unit displays, on the display unit, the series of images including the image from which the image output stop flag is deleted to cancel the inhibition of output by the image determining unit, except for an image with the image output stop flag.

7. The image display apparatus according to claim 1, wherein the display unit displays a time bar indicative of a temporal position of a display image, and the display control unit enlarges the time bar indicative of the temporal positions of the series of images except for one or more images inhibited to be output by the image determining unit to the same length as that of a basic time bar indicative of temporal positions of the images included in the series of images, and displays the enlarged time bar on the display unit.

8. The image display apparatus according to claim 1, wherein the display unit displays a bar indicative of the number of images displayed, and the display control unit enlarges the bar indicative of the number of images displayed in the series of images except for one or more images inhibited to be output by the image determining unit to the same length as that of a basic bar indicative of the number of displayed images included in the series of images, and displays the enlarged bar on the display unit.

9. The image display apparatus according to claim 1, wherein a pixel region on the imaging device is an effective pixel region contributing to image capture, and the black region where optical rays do not reach in the pixel region is in the effective pixel region.

10. The image display apparatus according to claim 1, wherein the black region is optical black of the imaging device.

* * * * *